| (12) United States Patent<br>Davis et al. | (10) Patent No.: US 10,197,571 B2<br>(45) Date of Patent: Feb. 5, 2019 |
|---|---|

(54) ENZYME DETECTION DEVICE

(71) Applicant: Mologic Limited, Thurleigh, Bedfordshire (GB)

(72) Inventors: Paul Davis, Sharnbrook (GB); Gita Parekh, Milton Keynes (GB)

(73) Assignee: Mologic Limited, Bedfordshire (GB)

( * ) Notice: Subject to any disclaimer, the term of this patent is extended or adjusted under 35 U.S.C. 154(b) by 829 days.

(21) Appl. No.: 14/395,775

(22) PCT Filed: Apr. 22, 2013

(86) PCT No.: PCT/GB2013/051008
§ 371 (c)(1),
(2) Date: Oct. 20, 2014

(87) PCT Pub. No.: WO2013/156795
PCT Pub. Date: Oct. 24, 2013

(65) Prior Publication Data
US 2015/0160219 A1 Jun. 11, 2015

(30) Foreign Application Priority Data
Apr. 20, 2012 (GB) .................................. 1206976.1

(51) Int. Cl.
| G01N 33/50 | (2006.01) |
| G01N 33/573 | (2006.01) |
| C12Q 1/37 | (2006.01) |
| G01N 33/543 | (2006.01) |
| G01N 33/58 | (2006.01) |

(52) U.S. Cl.
CPC ............. *G01N 33/573* (2013.01); *C12Q 1/37* (2013.01); *G01N 33/543* (2013.01); *G01N 33/581* (2013.01); *G01N 2333/948* (2013.01); *G01N 2333/966* (2013.01); *G01N 2333/96494* (2013.01)

(58) Field of Classification Search
None
See application file for complete search history.

(56) References Cited

U.S. PATENT DOCUMENTS

| 6,342,349 B1 * | 1/2002 | Virtanen ............. B01J 19/0046 |
| | | 435/6.11 |
| 7,425,425 B2 * | 9/2008 | Lopez-Calle ............ C12Q 1/25 |
| | | 435/23 |
| 8,592,167 B2 * | 11/2013 | Davis ...................... C12Q 1/37 |
| | | 435/7.1 |
| 2006/0003394 A1 | 1/2006 | Song |

FOREIGN PATENT DOCUMENTS

| GB | 2437311 A | 10/2007 |
| GB | 2452076 A * | 2/2009 ............... C12Q 1/37 |
| GB | 2454672 A | 5/2009 |
| GB | 2471015 A | 12/2010 |
| WO | WO-2009/024805 A1 | 2/2009 |

OTHER PUBLICATIONS

Diamandis et al., Immunoassay, The Avidin-Biotin System, Chapter 11, pp. 237-255, 1996.*
International Search Report and Written Opinion for PCT/GB2013/051008 dated Jul. 4, 2013.
Search Report for GB1206976.1 dated Aug. 8, 2012.
Dupont, D., et al., "A New Approach to Monitoring Proteolysis Phenomena Using Antibodies Specifically Directed Against the Enzyme Cleavage Site on its Substrate", Analytical Biochemistry 317 (2003) 240-246.
Gustafson, et al., "Synthesis and Characterization of a Matrix-Metalloproteinase Responsive Silk-Elastinlike Protein Polymer", Bio Macromolecules, 2013, 14, 618-625.
Hefle, S., et al., "Validated sandwich enzyme-linked immunosorbent assay for casein and its application retail and milk-allergic complaint foods", Abstract, Nov. 2, 2014.

* cited by examiner

*Primary Examiner* — Gary Counts
(74) *Attorney, Agent, or Firm* — Andrus Intellectual Property Law, LLP

(57) ABSTRACT

Described herein is an enzyme detection device for detecting or measuring the presence in a test sample of the activity of an enzyme capable of cleaving a substrate. Also provided are methods for detecting enzyme activity, in particular the presence in a test sample of an enzyme capable of cleaving a substrate, and methods for determining the level or amount of such an enzyme in a test sample.

19 Claims, 13 Drawing Sheets

Specification includes a Sequence Listing.

| μg/ml MMP8 | Test line | PA line3 | PA line2 | PA line1 |
|---|---|---|---|---|
| 100 | 6 | 2 | 3 | 3 |
| 50 | 6 | 2 | 3 | 3 |
| 25 | 5 | 2 | 3 | 4 |
| 12.5 | 4 | 2 | 3 | 4 |
| 6.25 | 3 | 2 | 4 | 7 |
| 3.125 | 2 | 2 | 4 | 8 |
| 1.56 | 2 | 2 | 7 | 10 |
| 0 | 2 | 2 | 6 | 10 |

| Component | Size | Position from datum point |
|---|---|---|
| Backing card (81) | 75mm | 0mm |
| Nitrocellulose membrane (82) | 25mm | 16mm |
| Conjugate pad (83) | 10mm | 7mm |
| Buffer pad (84) | 11mm | 0mm |
| Absorbent pad (87) | 23mm | 52mm |
| Double sided tape (85) | 5mm | 16mm |
| Sample pad/blood separator pad (86) | 7mm | 16mm |

| | Cut-off (ng/ml) |
|---|---|
| 1 CS | 250-500 |
| 2 CS | 125-250 |
| 3 CS | 250-500 |
| 5 CS | 31.25-62.5 |
| 7 CS | <31.25 |

ENZYME DETECTION DEVICE

This application is a 371 national stage application of PCT/GB2013/051008, filed Apr. 22, 2013, which claims priority to GB 1206976.1, filed Apr. 20, 2012. The entire contents of each of these applications are hereby incorporated by reference.

SEQUENCE LISTING

The instant application contains a Sequence Listing which has been submitted in ASCII format via EFS-Web and is hereby incorporated by reference in its entirety. Said ASCII copy, created on Feb. 9, 2015, is named P 114939 US 00_ST 25 .txt and is 4 KB in size.

FIELD OF THE INVENTION

The present invention relates to an enzyme detection device, particularly although not exclusively, a device for detecting or measuring the presence in a test sample of the activity of an enzyme capable of cleaving a substrate. The invention also relates to methods for detecting enzyme activity, in particular the presence in a test sample of an enzyme capable of cleaving a substrate, and methods for determining the level or amount of such an enzyme in a test sample.

BACKGROUND TO THE INVENTION

Enzymes constitute a family of proteins involved in catalysing chemical reactions within living organisms. As a result of their importance, there are numerous situations in which it is necessary and/or beneficial to measure enzyme levels, and importantly, enzyme activity.

In particular, increases in enzyme activity have been found to correlate with specific conditions and/or diseases. For example up-regulated protease activity has been associated with many aspects of cancer progression. The measurement of enzyme activity in samples taken from individuals with a particular condition or suspected of having a specific condition or disease may therefore be useful for prognostic or diagnostic purposes.

Within the enzyme family, there are many classes of enzyme that act by facilitating substrate cleavage. For example, peptidases and proteases catalyse the hydrolysis of peptide bonds within their respective substrates. In the past, researchers have, in some cases, sought to measure this type of activity using kits or devices that measure release of a fragment or 'leaving group' from the initial enzyme substrate.

Assays based on this fundamental principle have been refined such that in some cases, inventors have described engineered substrate molecules linked to reporter moieties. Cleavage of the substrate by the enzyme to be detected, if present, leads to release of said reporter, which can be detected by a range of techniques available to those skilled in the art. An assay of this type is described for example in US2006/0003394.

Others have sought to develop assays for the measurement of enzyme activity based around the principle of discriminating between modified and unmodified forms of an enzyme substrate. In this regard, WO2009/024805 describes an enzyme detection device utilising a "substrate recognition molecule" (SRM) carrying a detectable label, wherein the SRM specifically binds to the enzyme substrate in either the unmodified or modified state.

Problems associated with the assays described to date include, in particular, the accuracy that can be achieved using the formats described. In particular, US2006/0003394 describes a kit wherein the enzyme-substrate mixture is applied to a chromatographic medium. Immobilisation of the substrate-reporter "reactive complex" at an upstream site occurs in the absence of enzyme whereas, in the presence of enzyme, cleavage of the reactive complex results in flow of the reporter to a downstream site. Since the enzyme, if present, can continue to cleave reactive complex immobilised at the upstream site, any signal generated by the presence of reporter at either site is subject to change with time, such that there is no clear endpoint to the reaction. This can create significant problems with the accuracy and reproducibility of data generated using this assay format.

SUMMARY OF THE INVENTION

In view of the numerous situations in which the measurement of enzyme activity would be useful or of benefit, it was an aim of the present inventors to develop a simple, robust device for the accurate detection of enzyme cleavage activity within a test sample.

In accordance with a first aspect of the invention, there is provided an enzyme detection device for detecting the presence in a test sample of cleavage activity of an enzyme capable of cleaving a substrate, the device comprising:
(i) an indicator molecule for adding to the test sample, said indicator molecule comprising
  (a) a cleavage site, which can be cleaved by said enzyme if said enzyme cleavage activity is present;
  (b) a first capture site; and
  (c) a detection region comprising a second capture site, wherein cleavage of the cleavage site results in release of a fragment of the indicator molecule comprising the detection region;
(ii) a first capture zone to receive the test sample, wherein the first capture zone comprises first capture molecules capable of binding to the first capture site of the indicator molecule but not the cleaved fragment of the indicator molecule comprising the detection region and wherein the indicator molecule is captured by binding of the first capture site to the first capture molecules thereby substantially preventing any subsequent cleavage of the cleavage site by the enzyme; and
(iii) a second capture zone to receive the test sample following contact of the test sample with the first capture zone, wherein the second capture zone comprises second capture molecules capable of binding to the second capture site of the indicator molecule, wherein the second capture zone is spatially separated from the first capture zone, and wherein detection of any cleaved indicator molecule via the detection region and bound via the second capture site to the second capture molecules, indicates the presence of cleavage activity of the enzyme in the test sample.

In use, the test sample is first contacted with the first capture zone, wherein the indicator molecule is captured by binding of the first capture site to the first capture molecules thereby substantially preventing any subsequent cleavage of the cleavage site by the enzyme, and subsequently contacted with the second capture zone wherein detection of any cleaved indicator molecule via the detection region and bound via the second capture site to the second capture molecules, indicates the presence of cleavage activity of the enzyme in the test sample.

The test sample for use in conjunction with the device of the invention may be any material known or suspected to contain an enzyme and may be derived from any source. In certain embodiments, the test sample may be derived from a biological source including fluids such as blood, saliva, urine, milk, fluid from a wound, ascites fluid, peritoneal fluid, amniotic fluid and so forth. In a preferred embodiment, the test sample is wound fluid and the device is used to detect enzyme activity, preferably protease activity, in the wound fluid as a means to assess the status and/or rate of healing of a wound. In a specific embodiment, the test sample is urine and the device is used to detect the activity of enzymes, in particular proteases, in the urine.

The test sample may be collected by any suitable means and presented in any form suitable for use with the present device including solid or liquid forms. Moreover, as part of obtaining the test sample from its original source, the sample may undergo one or more processing or pre-treatment steps prior to testing using the device of the invention. In one embodiment, a solid sample may be processed so as to produce a solution or suspension for testing. Moreover, in certain embodiments, the test sample may be stored, for example frozen at around −20° C., as a means of preserving the sample for any given length of time prior to testing using the device of the invention.

The device of the invention is for detecting the presence of cleavage activity of an enzyme. The device may therefore be used to measure indirectly whether an enzyme is (physically) present or absent in any given test sample. Alternatively, a test sample may be provided in which an enzyme is known to be present, and the cleavage activity of said enzyme may be measured using the device of the invention. For example, test samples containing a known amount of enzyme and one or more modulators or suspected modulators of enzyme activity may be used in conjunction with the present device. In one embodiment of the invention, the device is used to test potential modulators or inhibitors of enzyme cleavage activity.

The present device relies on use of an indicator molecule which is added to the test sample. Thus, in accordance with a second aspect of the invention, there is provided an indicator molecule for use in detecting the presence in a test sample of cleavage activity of an enzyme capable of cleaving a substrate, the indicator molecule comprising:
(a) a cleavage site, which can be cleaved by said enzyme if said enzyme cleavage activity is present;
(b) a first capture site; and
(c) a detection region comprising a second capture site, and wherein cleavage of the cleavage site results in release of a fragment of the indicator molecule comprising the detection region.

The indicator molecule of the present device comprises firstly a cleavage site which is selected such that it is cleaved specifically by the enzyme or enzymes to be detected, if said enzymes are present within the test sample. Cleavage of the indicator molecule at the cleavage site is essential to the functioning of the enzyme detection device as it results in release of a fragment of the indicator molecule comprising the detection region; this indicator molecule fragment is not bound by the first capture molecules within the first capture zone of the device. Detection of the released fragment within the second capture zone of the device is therefore indicative of enzyme cleavage activity in a test sample.

The cleavage site may be any site at which an enzymatically-cleavable bond is present. For example, this bond may be present between neighbouring residues of the indicator molecule. Such residues may be selected from nucleotides, monosaccharides, and amino acids. In a preferred embodiment of the invention, the cleavage site is a specific peptide bond located between two amino acid residues.

In a further preferred embodiment of the invention, the cleavage site is located within a substrate region of the indicator molecule. Said substrate region may comprise a peptide, a protein, a carbohydrate, a lipid or a nucleic acid. In certain embodiments, the substrate region of the indicator molecule may be engineered such that it comprises the enzyme's natural substrate or a portion thereof, such that the enzyme is presented with its native cleavage site in its native state. In certain other embodiments, the indicator molecule may be engineered such that it comprises an artificial or non-native cleavage site and/or substrate region. For example, the substrate region may be engineered or mutated such that the rate of cleavage activity or specificity of cleavage activity exhibited by the enzyme is increased (or decreased) relative to the rate and/or specificity of cleavage activity of the enzyme measured under comparable conditions against the enzyme's natural substrate.

The enzyme or enzymes to be detected using the device described herein must be capable of cleaving substrates. This activity is required in order for the indicator molecule to be split into at least two separate fragments, one of which consists of or comprises the detection region. Thus, in preferred embodiments of the present invention, the enzyme or enzymes to be detected are selected from the following categories:—oxidoreductases, hydrolases and lyases, and include the subcategories of protease, peptidase, lipase, nuclease, carbohydrase, phosphatase, sulphatase, neuraminidase, esterase, DNAse, and RNAse.

In preferred embodiments, the device of the invention is used to detect enzyme activity in fluids derived from wounds. In such embodiments, the enzymes to be detected are preferably proteases, and in particular matrix metalloproteases (MMPs) and human neutrophil-derived elastase (HNE). In a preferred embodiment, the enzyme to be detected is a cathepsin, in particular cathepsin G.

In further embodiments, the device of the invention is used to detect enzyme activity in a urine sample collected from a subject. In such embodiments, the enzymes to be detected are preferably proteases and in particular, matrix metalloproteases (MMPs) and human neutrophil-derived elastase (HNE).

In certain embodiments of the invention, the cleavage site and/or substrate region of the indicator molecule may be relatively non-specific such that the cleavage site is capable of being recognised or acted on by more than one enzyme or subcategory of enzyme as defined above. For example, a simple peptide substrate may be subject to cleavage by both proteases and peptidases. In embodiments wherein the cleavage site is recognised or acted on by more than one enzyme, the device may be used to detect the presence in a test sample of any of such enzymes capable of cleaving the indicator molecule.

In other embodiments of the invention, the cleavage site and/or substrate region of the indicator molecule may be highly specific such that only one enzyme or one sub-type of enzyme is capable of recognising and cleaving the cleavage site. In this context, a sub-type is defined as a classification of enzymes falling within any of the subcategories defined above. For example, the cleavage site may be recognised by a single protease or sub-type of proteases. Protease subtypes may include the following:—serine proteases; threonine proteases; cysteine proteases; aspartate proteases; metalloproteases and glutamic acid proteases. In such embodiments, the device may be tailored to the detection of a single enzyme or single enzyme subtype within a test sample.

The indicator molecule of the device may also comprise multiple cleavage sites wherein cleavage at any one of the cleavage sites results in release of an indicator molecule fragment consisting of or comprising the detection region. In the context of the present invention, the term 'multiple' means at least two, at least three, at least four, and so forth.

In certain embodiments, the indicator molecule includes between 2, 3, 4, 5 and 10, 11, 12, 13, 14, 15, 16, 17, 18, 19, 20, 25, 50, 100, 500 or 1000 cleavage sites. In some embodiments, the indicator molecule includes between 2 and 5, 6, 7, 8, 9 or 10 cleavage sites.

In one embodiment, the multiple cleavage sites may all be identical. In this configuration, the repeated cleavage site may be relatively non-specific or may be highly specific for one enzyme or enzyme subtype as defined above. Moreover, use of an indicator molecule of this type may help to increase the sensitivity of the enzyme detection device by providing a means to increase the concentration of cleavage sites present within the test sample.

In other embodiments, the indicator molecule may comprise multiple cleavage sites wherein there are at least two different cleavage sites present within the same indicator molecule. In preferred embodiments of the invention, the indicator molecule may comprise at least three, at least four, at least five, and up to at least 8 different cleavage sites.

In a further preferred embodiment, the different cleavage sites are recognised by different enzymes or different categories, subcategories or subtypes of enzymes as defined above, such that the device of the invention can be used to detect the activity of multiple different enzymes.

The activities may be grouped, such that the detection of enzyme activity gives a useful result. For example, a group of enzymes may be involved in a disease state such that detection of the relevant activity of one or more of the enzyme group is diagnostically useful.

Use of multiple cleavage sites (whether identical or non-identical) may be particularly useful for situations in which very low levels of enzyme activity are to be detected in a test sample. For example, an indicator molecule having multiple cleavage sites as defined above may be used to detect enzyme activity in a urine sample containing low levels of protease.

In addition to a cleavage site, the indicator molecule of the invention comprises a first capture site. The first capture site mediates binding of the indicator molecule to a first capture molecule present within the first capture zone of the device. Thus, the first capture site is the portion of the indicator molecule responsible for retaining or localising the indicator molecule within the first capture zone of the device. Following cleavage of the indicator molecule, the first capture site may remain intact or substantially intact, such that the site is still recognised and bound by a first capture molecule present within the first capture zone of the device. Under these circumstances, both intact indicator molecules and any cleaved fragments of indicator molecules comprising the first capture site will be bound to first capture molecules within the first capture zone of the device.

Alternatively, cleavage of the indicator molecule may lead to the disruption or destruction of the first capture site such that only intact (i.e. those that have not been acted upon by the enzyme) indicator molecules are able to bind to the first capture molecules located within the first capture zone of the device.

In certain embodiments, the first capture site of the indicator molecule may be contained in the same region of the indicator molecule as the cleavage site. In the context of the present invention, a 'region' defines a portion or domain of the indicator molecule that may contain multiple 'sites'. The cleavage site and the first capture site may form discrete sites within a substrate region of the indicator molecule. Alternatively, the cleavage site and first capture site may form overlapping sites within a substrate region of the indicator molecule. Wherein the cleavage site and first capture site overlap, it is more likely that cleavage of the indicator molecule will result in disruption or destruction of the first capture site (as discussed above).

As noted above, the substrate region may be a peptide, a protein, a carbohydrate, a lipid or a nucleic acid. In a preferred embodiment of the indicator molecule, the cleavage site and first capture site are defined by discrete amino acids or groups of amino acids within a peptide or protein substrate region. In a further preferred embodiment of the invention, the cleavage site and first capture site are defined by overlapping amino acid residues within a peptide or protein substrate region. As used herein the term "peptide" is intended to mean a length of amino acids of no more than about 20, 30, 40 or 50 amino acids.

Alternatively, the first capture site may be present in a region of the indicator molecule which is separate to the region in which the cleavage site is located. Thus, in certain embodiments of the invention, the first capture site may be present within a first capture region, and the cleavage site may be present within a separate substrate region of the indicator molecule. In embodiments wherein the first capture site is in a separate region of the indicator molecule to the cleavage site, the first capture site may comprise materials or residues entirely distinct from those found in the region of the molecule containing the cleavage site. For example, the substrate region may comprise amino acid residues whilst the first capture site may comprise or consist of a biotin moiety. Moreover, in embodiments wherein the indicator molecule comprises separate regions bearing the cleavage site and first capture site, said regions may be associated by any means known to one of skill in the art. In a preferred embodiment, said regions may be associated via a direct covalent linkage. Moreover, said regions may be immediately adjacent or may be separated by a linker or spacer, for example, a polyethylene glycol moiety.

In all embodiments of the invention, irrespective of whether the first capture site is within the same or different region of the indicator molecule to the cleavage site, binding of the first capture site of the indicator molecule to a first capture molecule present within the first capture zone of the device substantially prevents any subsequent cleavage of the cleavage site by the enzyme. In embodiments wherein the indicator molecule comprises multiple cleavage sites, binding of the first capture site of the indicator molecule to a first capture molecule substantially prevents any further enzyme cleavage at any of the cleavage sites. In this context, "substantially prevents" means that once the indicator molecule is bound to the first capture molecule, there is no further cleavage of indicator molecule sufficient to cause a (significant) detectable change in the proportion of cleaved versus uncleaved indicator molecule measured using the device over or after a defined period of time. This feature is integral to the use of the present device for the purposes of achieving a reliable, accurate "end-point" assay as is discussed in greater detail below.

Once the indicator molecule is bound via the first capture site to a first capture molecule of the device, cleavage may be substantially prevented as a result of the binding interaction physically blocking enzyme access to the cleavage site. Access to the cleavage site may be blocked upon binding of the indicator molecule to the first capture molecule as a result of the overlap or close proximity between the cleavage site and the first capture site. Alternatively, binding of the indicator molecule to the first capture molecule may not result in direct blocking of the cleavage site but may substantially prevent enzyme access to this site by virtue of a conformational change in the indicator molecule resulting in steric hindrance around the cleavage site.

It is preferable within the context of the present invention for the indicator molecules to bind to the first capture molecules with relatively high affinity. In preferred embodiments, the dissociation rate ($k_d$) for the indicator molecule will be relatively low and preferably between 0M and $1\times10^{-7}$M (depending on the sensitivity required of the assay). In a particularly preferred embodiment of the invention, the dissociation rate for the indicator molecule will be between $1\times10^{-15}$M and $1\times10^{-9}$M.

In certain embodiments of the invention, such a binding interaction may be achieved as a result of direct binding of the first capture site of the indicator molecule to the first capture molecule present in the first capture zone of the device. In this context, direct binding means binding of the indicator molecule to the first capture molecule without any intermediary.

In a preferred embodiment of the invention, the first capture site of the indicator molecule and the first capture molecule present in the first capture zone of the device are two halves of a binding pair. In this context, a binding pair consists of two molecules or entities capable of binding to each other. In a preferred embodiment of the invention, the binding interaction is specific such that each member of the binding pair is only able to bind its respective partner, or a limited number of binding partners. Moreover, as detailed above, it is preferable for the binding pair to exhibit relatively high affinity. The binding pair may be a binding pair found in nature or an artificially generated pair of interacting molecules or entities.

In a further preferred embodiment of the invention, the first capture site of the indicator molecule and the first capture molecule are two halves of a binding pair wherein the binding pair is selected from the following:—an antigen and an antibody or antigen binding fragment thereof; biotin and avidin, streptavidin, neutravidin or captavidin; an immunoglobulin (or appropriate domain thereof) and protein A or G; a carbohydrate and a lectin; complementary nucleotide sequences; a ligand and a receptor molecule; a hormone and hormone binding protein; an enzyme cofactor and an enzyme; an enzyme inhibitor and an enzyme; a cellulose binding domain and cellulose fibres; immobilised aminophenyl boronic acid and cis-diol bearing molecules; and xyloglucan and cellulose fibres and analogues, derivatives and fragments thereof.

In a particularly preferred embodiment of the device of the invention, the binding pair consists of biotin and streptavidin. In a further particularly preferred embodiment of the invention, the first capture site of the indicator molecule comprises an epitope and the first capture molecule comprises an antibody, which specifically binds to the epitope present at the first capture site. In the context of the present invention, the term antibody covers native immunoglobulins from any species, chimeric antibodies, humanised antibodies, F(ab')$_2$ fragments, Fab fragments, Fv fragments, sFv fragments and highly related molecules such as those based upon antibody domains which retain specific binding affinity (for example, single domain antibodies).

In certain embodiments of the invention, binding of the first capture site of the indicator molecule to the first capture molecule of the device may be indirect. In the context of the present invention, "indirect binding" means binding mediated by some intermediate entity capable of bridging the indicator molecule and the first capture molecule, for example an "adaptor" capable of simultaneously binding the first capture site of the indicator molecule and the first capture molecule.

Wherein binding of the indicator molecule to the first capture molecule is indirect and mediated by an adaptor, it may be possible for a plurality of indicator molecules to bind to each first capture molecule. In this context, a plurality means at least two, at least three, at least four, and so forth. This may be achieved by the incorporation of a multivalent adaptor molecule, for example, a streptavidin molecule capable of simultaneous binding to multiple biotin-containing indicator molecules in addition to a first capture molecule consisting of or comprising biotin.

Embodiments of the device wherein a plurality of indicator molecules bind to each first capture molecule, may be used to achieve improved assay accuracy as described in greater detail below.

In addition to a cleavage site and a first capture site, the indicator molecule of the invention comprises a detection region comprising, consisting essentially of or consisting of a second capture site. The configuration of the indicator molecule is such that cleavage at the cleavage site leads to release of an indicator molecule fragment comprising the detection region. This indicator molecule fragment comprising the detection region is not recognised or bound by the first capture molecules within the first capture zone of the device. Instead, the second capture site within the detection region allows for capture of the released indicator molecule fragment within the second capture zone of the device of the invention by virtue of the binding interaction between the second capture site and the second capture molecules present within the second capture zone of the device.

The detection region of the indicator molecule may be attached to the cleavage site or the region of the indicator molecule containing the cleavage site by any suitable means. In one embodiment, attachment is via a direct covalent linkage. In an alternative embodiment, the detection region of the indicator molecule is attached to the region containing the cleavage site via a linker or carrier protein. In a preferred embodiment of the indicator molecule, the detection region and the region containing the cleavage site comprise, consist essentially of or consist of peptides, and the carrier protein comprises, consists essentially of or consists of bovine serum albumin. Through use of a carrier protein the relative amounts of detection region and region containing the cleavage site may be modified by controlling the number of each region attached to the carrier protein. The carrier protein thus also permits multiple detection regions and regions containing the cleavage site to be attached to each carrier protein. Thus, in some embodiments a larger number of detection regions may be attached to the carrier protein than regions containing the cleavage site. For example, the carrier protein may include a 2:1, 3:1, 4:1 or 5:1 ratio of detection regions to regions containing the cleavage site. This may improve the sensitivity of the device. The reverse may apply in other embodiments.

In one embodiment of the invention, binding of the second capture site within the detection region to the second capture molecules within the second capture zone of the device may be direct i.e. without any intermediary. In a preferred embodiment, the second capture site and second capture molecules are two halves of a binding pair wherein a "binding pair" is as defined above. The binding pair may be selected from the following:—an antigen and an antibody or antigen binding fragment thereof; biotin and avidin, streptavidin, neutravidin or captavidin; an immunoglobulin (or appropriate domain thereof) and protein A or G; a carbohydrate and a lectin; complementary nucleotide sequences; a ligand and a receptor molecule; a hormone and hormone binding protein; an enzyme cofactor and an enzyme; an enzyme inhibitor and an enzyme; a cellulose binding domain and cellulose fibres; immobilised aminophenyl boronic acid and cis-diol bearing molecules; and xyloglucan and cellulose fibres and analogues, derivatives and fragments thereof.

In a particularly preferred embodiment of the invention, the binding pair consists of biotin and streptavidin. In a further particularly preferred embodiment of the invention, the second capture site of the indicator molecule comprises an epitope distinct from any epitope found at the first capture site and the second capture molecule comprises an antibody, which specifically binds to the epitope present at the second capture site. The term antibody is as defined above.

In another embodiment of the invention, binding of the second capture site to the second capture molecules within the second capture zone of the device is indirect, for example mediated by an adaptor capable of simultaneously binding the second capture site of the indicator molecule and the second capture molecule. Wherein binding of the indicator molecule to the second capture molecule is indirect and mediated by an adaptor, it may be possible for a plurality of cleaved indicator molecule fragments to bind to each second capture molecule. In a preferred embodiment of the invention, both the second capture site of the detection region of the indicator molecule and second capture molecules of the device comprise biotin, and the adaptor molecule mediating the indirect binding is multivalent streptavidin or a derivative thereof.

The detection region of the indicator molecule may be any substance or moiety suitable for detection by any means available to those skilled in the art. In one embodiment of the invention, the detection region itself may comprise a reporter moiety wherein a reporter moiety is defined herein as any moiety capable of signal generation or production. In a preferred embodiment of the invention, the reporter moiety is selected from the following:—a gold particle; a chromogen; a luminescent compound; a fluorescent molecule; a radioactive compound; a visible compound; a liposome or other vesicle containing signal producing substances; an electroactive species; or a combination of enzyme and its substrate. A suitable enzyme-substrate combination for use as a reporter moiety may be the enzyme alkaline phosphatase and the substrate nitro blue tetrazolium-5-bromo-4-chloro-3-indolyl phosphate. In a particularly preferred embodiment of the invention, the reporter moiety is a gold particle.

Alternatively or in addition to the above embodiments, the device may comprise one or more reporter molecule(s) bound or capable of binding to the detection region of the indicator molecule, and detection may be carried out using the signal generated by the reporter molecule(s). In certain embodiments, the reporter molecule may bind to the detection region of the indicator molecule at a specific "detection site", which is distinct and spatially separated from the second capture site present within the detection region. The detection site may comprise a group of residues positioned directly adjacent or in close proximity to the second capture site. Alternatively, the detection site may comprise a discrete portion of the indicator molecule spatially separated from the second capture site, for example by virtue of a linker or spacer region.

In embodiments of the device wherein the second capture site binds directly to the second capture molecules, it may be advantageous for the detection site to be spatially separated from the second capture site so as not to impede simultaneous binding of the second capture molecule (via the second capture site) and the reporter molecule (via the detection site) to the indicator molecule.

Wherein the detection region comprises a detection site and a second capture site, in certain embodiments, these sites may be identical. Under such circumstances, the binding moiety of the second capture molecule that mediates binding to the second capture site of the indicator molecule may be identical to the binding moiety of any reporter molecule that mediates binding to the detection site of the indicator molecule. In a preferred embodiment, the detection site and second capture site comprise the same epitope and the second capture molecules and any reporter molecules comprise an antibody which specifically binds to said epitope.

In alternative embodiments, the detection site and second capture site may be different. Furthermore, despite the fact that the detection site and second capture site are both defined as present within the "detection region" of the indicator molecule, these two sites may comprise or consist of different chemical entities conjoined so as to form the detection region of the molecule. For example, the second capture site may comprise a first peptide antigen whilst the detection site may comprise a biotin moiety. In a preferred embodiment of the invention, the detection site comprises an epitope, distinct from any epitope present within the first capture site and second capture site, and the reporter molecule comprises an antibody which specifically binds to said epitope.

In certain other embodiments of the invention, the reporter molecule may bind to the detection region of the indicator molecule via the second capture site provided that binding of the reporter molecule to the second capture site does not impair the ability of the second capture site to bind second capture molecules in the second capture zone of the device.

The reporter molecule of the invention may comprise any reporter moiety capable of generating a signal for detection purposes. In preferred embodiments of the invention, the reporter moiety is selected from the following: a gold particle; a chromogen; a luminescent compound; a fluorescent molecule; a radioactive compound; a visible compound; a liposome or other vesicle containing signal producing substances; an electroactive species; or a combination of enzyme and its substrate.

Binding of the reporter molecule to the indicator molecule may be indirect and mediated by an adaptor capable of simultaneously binding the detection region and the reporter molecule.

In embodiments of the invention wherein the reporter molecule binds to the indicator molecule by virtue of an adaptor molecule, the adaptor may be pre-complexed with the detection region prior to the addition of the test sample to the indicator molecule, provided that the adaptor does not prevent cleavage of the indicator molecule.

The adaptor may be any material or molecule capable of mediating the indirect interaction of the detection region of the indicator molecule with the reporter molecule. In a preferred embodiment, the adaptor is streptavidin and the detection region comprises biotin. The adaptor may also be an "adaptor binding pair" wherein said binding pair comprises:
(i) a first member capable of binding to the detection region of the indicator molecule; and
(ii) a second member capable of binding to the first member of the pair and to the reporter molecule. In a particularly preferred embodiment of the invention, the detection region of the indicator molecule comprises biotin, the first member of the adaptor binding pair is avidin or streptavidin, the second member of the adaptor binding pair is biotin, and the reporter molecule comprises a moiety capable of binding biotin.

The inclusion of an adaptor molecule or an adaptor binding pair may facilitate the binding of multiple reporter molecules to each indicator molecule. For example, the use of multivalent streptavidin as the adaptor will allow for simultaneous binding of both a biotin-containing indicator molecule in addition to multiple biotin-containing reporter molecules.

In embodiments of the device wherein the reporter molecule is bound to the detection region of the indicator molecule via an adaptor or adaptor binding pair, this same adaptor or adaptor binding pair may serve to mediate indirect binding of the second capture site to the second capture molecules present in the second capture zone of the device.

In preferred embodiments, the second capture site of the indicator molecule comprises biotin and binds an adaptor comprising streptavidin. The streptavidin adaptor mediates binding to both biotin-containing reporter molecules and second capture molecules also comprising biotin. Thus, the same adaptor exhibits three-way binding to link the detection region of the indicator molecule to both the reporter molecule and the second capture molecule in the second capture zone of the device.

In order for the device to function as intended, the first capture zone must be spatially separated from the second capture zone. This spatial separation must be such that it allows the test sample combined with the indicator molecule to first be brought into contact with the first capture molecules within the first capture zone, and subsequently contacted with the second capture molecules within the second capture zone. In one embodiment, the first capture zone and second capture zone may consist of distinct compartments within an assay test kit requiring manual transfer by the user of test sample from one compartment to the other. The first and second capture zones may be found on separate solid supports in certain embodiments e.g. in separate columns or on beads found in distinct physical locations.

In a preferred embodiment of the invention, the device is configured as a flow device and the first capture zone and second capture zone are present at sequential locations along a chromatographic medium. The chromatographic medium may be mounted on a solid support. In a particularly preferred embodiment of the invention, the device may be configured as a lateral flow device but may also be configured as a vertical flow device for example. The device may take the form of a test strip in certain embodiments.

The first capture zone may be defined by the immobilization therein or thereon of first capture molecules capable of binding to the first capture site of any intact indicator molecules and, in certain embodiments, cleaved fragments of indicator molecules containing an intact first capture site. The second capture zone may be defined by the immobilization therein or thereon of second capture molecules capable of binding to any cleaved fragments of indicator molecule containing the detection region of the molecule, if present. Immobilization of first capture molecules and/or second capture molecules may be achieved by any suitable means. Wherein the device is a flow device comprising a chromatographic medium, the capture molecules may be immobilized by directly binding to the medium or immobilized indirectly via binding to a carrier protein associated with the medium.

The test sample may be applied to the chromatographic medium at a site upstream from the first capture zone such that it is drawn, for example by capillary action, through the first capture zone followed by the second capture zone. The chromatographic medium may be made from any material through which a fluid is capable of passing, such as a fluidic channel or porous membrane. In a preferred embodiment of the invention, the chromatographic medium comprises a nitrocellulose strip or membrane.

Wherein the device of the invention comprises reporter molecules capable of binding to the detection region of the indicator molecule, as described above, the device may additionally comprise a third capture zone comprising third capture molecules. The third capture zone is spatially separated from the first and second capture zones.

In certain embodiments, the third capture molecules within the third capture zone may bind any reporter molecules that are not bound to indicator molecules, or fragments thereof. In preferred embodiments, the third capture molecules may be antibodies capable of recognising an epitope within the reporter molecule, wherein the epitope is distinct from any epitope found within the indicator molecule. Detection of reporter molecule binding to the third capture molecules within the third capture zone may be used to determine the existence of functional reporter molecules within the device.

In further embodiments of the invention, the device may comprise, in addition to a reporter molecule, one or more "control reporter molecule(s)". Typically, the control reporter molecule(s) will comprise the same reporter moiety as the reporter molecule, but will not bind to the detection region of the indicator molecule. Such control reporter molecule(s) may be used to indirectly assess the presence and/or functioning of the reporter molecule within the device. Under these circumstances, the device may also comprise a third capture zone, spatially separated from the first and second capture zones, comprising third capture molecules, wherein said third capture molecules are capable of binding the control reporter molecule, if present. In preferred embodiments, the third capture molecules are antibodies capable of recognising an epitope within the control reporter molecule, wherein the epitope is distinct from any epitope found within the indicator molecule or reporter molecule. Detection of control reporter molecule binding to the third capture molecules within the third capture zone may be used to indirectly assess the existence of functional reporter molecules within the device.

The enzyme detection device above is for use in detecting or measuring the presence in a test sample of the activity of an enzyme capable of cleaving a substrate.

Thus, in accordance with a third aspect of the invention there is provided herein a method for detecting the presence in a test sample of an enzyme capable of cleaving a substrate, the method comprising the steps of:
(i) providing an enzyme detection device comprising an indicator molecule for adding to the test sample, said indicator molecule comprising
(a) a cleavage site, which can be cleaved by said enzyme if said enzyme cleavage activity is present;

(b) a first capture site; and
(c) a detection region comprising a second capture site, wherein cleavage of the cleavage site results in release of a fragment of the indicator molecule comprising the detection region;
a first capture zone to receive the test sample, wherein the first capture zone comprises first capture molecules capable of binding to the first capture site of the indicator molecule but not the cleaved fragment of the indicator molecule comprising the detection region; and
a second capture zone to receive the test sample following contact of the test sample with the first capture zone, wherein the second capture zone comprises second capture molecules capable of binding to the second capture site of the indicator molecule
and wherein the second capture zone is spatially separated from the first capture zone;
(ii) providing a test sample;
(iii) adding the indicator molecules of the device to the test sample under conditions in which the enzyme, if present, can cleave the substrate region;
(iv) bringing the test sample into contact with the first capture molecules of the device such that any intact indicator molecules, if present, are bound to the first capture molecules within the first capture zone and wherein binding of the indicator molecules to the first capture molecules substantially prevents any subsequent cleavage of the cleavage site of the indicator molecule by the enzyme;
(v) bringing the test sample into contact with the second capture molecules of the device such that any fragments of cleaved indicator molecule comprising the detection region are bound, via the second capture site, by the second capture molecules; and
(vi) detecting the presence or absence or level of fragments of cleaved indicator molecule comprising the detection region in the second capture zone via the detection region in order to determine the presence of enzyme in the test sample.

The method detailed above involves use of an enzyme detection device as described in detail elsewhere herein. All embodiments described in respect of the enzyme detection device and indicator molecule of the invention apply mutatis mutandis to these aspects of the methods of the invention and therefore are not repeated for reasons of conciseness.

The method of the invention requires addition of the indicator molecules of the device to the test sample under conditions in which the enzyme, if present, can cleave the substrate region. The conditions used for carrying out the method may depend on the enzyme(s) of interest to be detected and may include variations in parameters such as time of incubation of the indicator molecule and test sample, temperature, pH. Furthermore, the conditions may be adjusted so as to influence the sensitivity of the assay; for example, a longer incubation time may increase the proportion of cleaved indicator molecules in the test sample. The device and methods of the invention may be utilised in order to optimise assay conditions for an enzyme of interest in certain embodiments.

The amount or concentration of indicator molecules added to the test sample may also be varied depending on the enzyme(s) to be detected. It is preferable for sufficient indicator molecules to be added to the test sample such that the enzyme substrate is present in excess.

It is important for the functioning of the device that incubation of the indicator molecule with the test sample is carried out prior to bringing the test sample plus indicator molecule into contact with the first capture molecules of the device. In one embodiment, the indicator molecule is present within the device used to collect the test sample.

Once the indicator molecules are exposed to the first capture molecules and are thus bound, cleavage of the cleavage site by the indicator molecule is substantially prevented. Furthermore, as already discussed above, in a preferred embodiment of the invention, the indicator molecule binds via the first capture site to the first capture molecules of the device with high affinity. In particular, it is preferable for the first capture molecule to have a higher association rate ($k_a$) and a lower dissociation rate ($k_d$) for the indicator molecule than the enzyme has for the indicator molecule. Taken together, these features help to ensure that there is no further enzymatic cleavage of the indicator molecule once the test sample has been brought into contact with the first capture molecules within the first capture zone. Thus, the present device can be used as a reliable end-point assay.

The assay results obtained by carrying out the method of the invention are also affected by the relationship between the quantity of first capture molecules present within the first capture zone of the device and the quantity of indicator molecules added to the test sample. In one embodiment of the invention, there are sufficient first capture molecules present so as to capture the total quantity of indicator molecules in the test sample in the first capture zone should no enzyme cleavage take place. The quantity of first capture molecules required to capture all the indicator molecules, or the quantity of indicator molecules that will saturate all the first capture molecule binding sites within the first capture zone of the device can readily be determined experimentally.

If there are fewer first capture molecules than needed to capture all the indicator molecules, any unbound or "free" intact indicator molecules in the first capture zone may be transferred to the second capture zone. The presence of intact indicator molecules in the second capture zone of the device may give rise to false positive results if detected within this zone. However, depending on the degree of assay sensitivity required, some degree of "leakage" of intact indicator molecules into the second capture zone may be tolerable. Moreover, this "leakage" may be measured and taken into account by virtue of an appropriate control reaction.

In circumstances wherein multiple indicator molecules may bind to each first capture molecule, for example wherein binding between the molecules is indirect and mediated by an adaptor, it may be possible to include fewer first capture molecules in the first capture zone and retain a high level of sensitivity by virtue of minimal intact indicator molecule "leakage" into the second detection zone.

The role of the first capture molecules is primarily to retain any intact indicator molecule within the first capture zone of the device. Binding of the indicator molecule to the first capture molecules is mediated by the first capture site on the indicator molecule. If the indicator molecule is cleaved, any portion or fragment containing the first capture site may still bind to the first capture molecules; however, in certain embodiments of the invention, cleavage of the indicator molecule may result in disruption or destruction of the first capture site such that only the intact indicator molecule is able to bind to the first capture molecules.

In order to retain the intact indicator molecule, and possibly any cleaved fragments thereof bearing the first capture site, the first capture molecules must be localised within the first capture zone such that they are not transferred to the second capture zone together with the test sample. Localisation may be achieved via binding of the first capture molecules to a solid support. In a preferred embodiment of the invention, the device is a flow device and the first capture molecules are immobilized at a discrete location along the long axis of the chromatographic medium. Immobilization of the first capture molecules may be achieved by any suitable means available to one of skill in the art.

After the test sample has been brought into contact with the first capture zone, and any intact indicator molecules, if present, have bound to the first capture molecules therein, the test sample is then transferred to the second capture zone. If the enzyme to be detected is present in the test sample and has therefore cleaved the indicator molecule, fragments of the indicator molecule comprising the detection region will be transferred into this zone. These fragments will be localised or retained within the second capture zone by virtue of binding of the second capture site within the detection region to the second capture molecules present within this zone. Localisation may be achieved via binding of the second capture molecules to a solid support. In a preferred embodiment of the invention, the device is a flow device and the second capture molecules are immobilized at a discrete location along the long axis of the chromatographic medium spatially separated from the first capture molecules of the first capture zone. Immobilization of the second capture molecules may be achieved by any suitable means available to one of skill in the art.

Thus, by detecting the presence or absence or level of fragments of cleaved indicator molecule comprising the detection region in the second capture zone via the detection region, the presence of enzyme activity can be determined. More specifically, if signal is generated at the second detection zone, enzyme activity is present in the test sample.

In certain embodiments of the invention, the method may involve detecting both the presence of any intact indicator molecule at the first capture zone and any fragments of indicator molecule comprising the detection region at the second capture zone. In view of the existence of indicator molecule at one or other of these sites, an inverse relationship may typically exist between the signal generated at the first capture zone and signal generated at the second capture zone. Moreover, if a signal generated from the reporter associated with the intact indicator molecule is present at the first capture zone but no signal is detectable in the second capture zone, this indicates that no enzyme is present within the test sample.

Detection of the indicator molecule or cleaved fragment thereof may be carried out by the detection of a reporter moiety present within the detection region. As detailed above, said reporter moiety may be any signal-generating moiety, and measurement or detection of signal may be carried out using any suitable means known to those skilled in the art depending on the nature of the reporter, for example, low-power visual inspection, microscopy, or use of a photomultiplier tube connected to a computer read-out.

In preferred embodiments of the invention, detection of the intact indicator molecule or cleaved fragment thereof is carried out by the addition of a reporter molecule capable of binding to the detection region. Said reporter molecule may take any of the forms already described above and may associate with the detection region of the indicator molecule in any of the ways already detailed herein.

In embodiments wherein detection is performed using a separate reporter molecule, said reporter molecule may be added to the indicator molecule prior to the addition of the indicator molecule to the test sample. It is preferable that, under these circumstances, the reporter does not interfere with cleavage of the indicator molecule by the enzyme. Alternatively, the indicator molecule may be added to the test sample in the absence of reporter molecule and the reporter molecule is present or added at the time the test sample is exposed to the first capture molecules within the first capture zone of the device. In a further alternative embodiment, the reporter molecule may be added after the test sample containing the indicator molecule has been exposed to both the first capture molecules within the first capture zone and the second capture molecules within the second capture zone.

As detailed above, in preferred embodiments of the invention, the device is configured as a flow device with the first capture zone and second capture zone defined by discrete locations along a chromatographic medium. The test sample may be exposed to the chromatographic medium at a site upstream from the first capture zone, for example a sample receiving zone. This site or zone may be defined by the presence of a sample pad to which the test sample is applied. In certain embodiments, this sample pad may perform a blood separator function such that certain components of the test sample, for example one or more types of blood cell, are retained within the material of the sample pad and thereby prevented from entering the chromatographic strip.

After application of the test sample to the sample receiving zone, the sample may flow through the first capture zone and into the second capture zone. The sample application zone may be separated from the first capture zone, for example by means of a soluble barrier, such that the test sample containing the indicator molecule is contacted with the chromatographic medium, for example a nitrocellulose strip, for a period of time before the sample flows through into the first capture zone. The chromatographic medium may also have attached thereto an adsorbent pad located downstream of the selective capture zone and detection zone. This may act as a reservoir to facilitate the flow of test sample through the zones of the chromatographic medium.

Reporter molecules may be added to the chromatographic medium after the test sample has been allowed to pass through or along the medium. In preferred embodiments, reporter molecules may be pre-associated with the chromatographic medium in a dried form at the time the test sample is applied to the medium. Once the test sample has been left for a period of time to flow through the first capture zone and second capture zone of the device, the reporter molecules may be reconstituted, for example by the addition of a suitable buffer, and thereafter allowed to flow through the chromatographic medium, such that any bound indicator molecule, or fragments thereof, are labelled by the subsequent binding of the reporter molecule.

The device of the invention may additionally comprise a third detection zone, as described above, comprising third capture molecules. In certain embodiments, the third capture molecules may bind any reporter molecules that are not bound to indicator molecules, or fragments thereof.

Wherein such a device is used, the methods of the present invention may involve additionally detecting the presence of any reporter molecule bound to third capture molecules within the third capture zone.

For embodiments wherein reporter molecules are used to detect the presence of indicator molecule, the device may also comprise control reporter molecules, as defined above. Such control reporter molecules may be added to the device at the same time as the reporter molecules are added to the device. Wherein the device is a flow device comprising a chromatographic medium, both the reporter molecule and the control reporter molecule may be pre-associated with the chromatographic medium in a dried form at the time the test sample is applied to the medium. Reconstitution of the reporter molecule, for example using a suitable buffer, may be accompanied by reconstitution of the control reporter molecule. Under these circumstances, the device of the invention may also comprise a third detection zone comprising third capture molecules capable of binding the control reporter molecule. Wherein such a device is used, the methods of the present invention may involve additionally detecting the presence of any control reporter molecules bound to third capture molecules within the third capture zone. This "control" readout may be important in order to confirm indirectly that reporter molecules are present and/or functional within the device.

Wherein the device of the invention is configured as a flow device comprising a chromatographic medium, the first and second capture zones and optionally the third detection or capture zone may be contained within a plastic housing, provided with means by which the reporter molecules immobilised at the different zones can be detected. For example, the plastic housing may contain windows permitting visual inspection of the signal generated by reporter molecules bound at the first, second and/or third capture zones. In certain embodiments, the plastic housing may hide the first capture zone from view such that only reporter molecules bound at the second capture zone and optionally the third capture zone can be detected (through visual inspection of a signal). This has the advantage that the end user sees a positive test line only in the presence of enzyme (at the second capture site).

If an adaptor is to be used to mediate any (one or more) of the following interactions:
(i) binding of the first capture site of the indicator molecule to the first capture molecules;
(ii) binding of the second capture site of the indicator molecule to the second capture molecules; and/or
(iii) binding of the reporter molecules to the detection region of the indicator molecule, this adaptor may be added to the indicator molecule prior to the addition of indicator molecule to the test sample i.e. it may be pre-complexed with the indicator molecule. Alternatively, the adaptor may be added to the device at the time the test sample containing indicator molecule is exposed to the first capture molecules within the first capture zone of the device or after the test sample has been exposed to both the first capture molecules within the first capture zone and the second capture molecules within the second capture zone (as appropriate).

The method incorporating the enzyme detection device of the current invention may be used to perform qualitative analysis of enzyme activity in a test sample as detailed above. Furthermore, the method may be adapted so as to perform quantitative or comparative analysis of the level(s) of enzyme activity in two or more test samples.

Therefore, in accordance with a further aspect of the invention there is provided herein a method of determining the amount of cleavage activity of an enzyme capable of cleaving a substrate in a first sample relative to the amount of cleavage activity of said enzyme in one or more additional samples comprising the steps of:
(i) providing an enzyme detection device comprising an indicator molecule for adding to the test sample, said indicator molecule comprising
  (a) a cleavage site, which can be cleaved by said enzyme if said enzyme cleavage activity is present;
  (b) a first capture site; and
  (c) a detection region comprising a second capture site, wherein cleavage of the cleavage site results in release of a fragment of the indicator molecule comprising the detection region;
a first capture zone to receive the test sample, wherein the first capture zone comprises first capture molecules capable of binding to the first capture site of the indicator molecule but not the cleaved fragment of the indicator molecule comprising the detection region; and
a second capture zone to receive the test sample following contact of the test sample with the first capture zone, wherein the second capture zone comprises second capture molecules capable of binding to the second capture site of the indicator molecule
and wherein the second capture zone is spatially separated from the first capture zone;
(ii) providing a first test sample;
(iii) adding the indicator molecules of the device to the first test sample under conditions in which the enzyme, if present, can cleave the cleavage site;
(iv) bringing the first test sample into contact with the first capture molecules of the device such that any intact indicator molecules, if present, are bound to the first capture molecules within the first capture zone and wherein binding of the indicator molecules to the first capture molecules substantially prevents any subsequent cleavage of the cleavage site of the indicator molecule by the enzyme;
(v) bringing the first test sample into contact with the second capture molecules of the device such that any fragments of cleaved indicator molecule comprising the detection region are bound, via the second capture site, by the second capture molecules;
(vi) detecting the presence and level of intact indicator molecule in the first capture zone and the presence and level of cleaved indicator molecule in the second capture zone;
(vii) repeating steps (i) to (vi) for the one or more additional test samples;
(viii) comparing the levels obtained for the first and one or more additional test samples in order to determine the relative levels of cleavage activity of any enzyme present in each test sample.

All embodiments described in respect of the earlier aspects of the present invention, namely the enzyme detection device, the indicator molecule and the method for detecting the presence in a test sample of an enzyme capable of cleaving a substrate, apply mutatis mutandis to this further method, and will therefore not be reiterated for reasons of conciseness.

This current aspect of the invention provides in addition, a method of using the enzyme detection device and associated indicator molecule described herein to determine the relative amounts of enzymatic cleavage activity in test samples based upon a comparison of two or more samples. In particular, the method requires detecting both the presence and level of intact indicator molecule in the first capture zone, and detecting the presence and level of cleaved indicator molecule in the second capture zone using any of the means detailed above. As mentioned previously, an inverse correlation will typically exist between these values, and in preferred embodiments, the ratio of these values will be calculated. The values obtained using one test sample are compared with the values obtained by performing the same method using one or more additional samples. From such a comparison, the relative amounts of enzyme cleavage activity in the respective test samples can readily be determined by one of skill in the art. For example, a higher ratio of signal at the second capture zone to signal at the first capture zone indicates a higher level of enzyme activity in the test sample.

This comparative analysis employing the method of the invention may be used for a variety of purposes. Firstly, measuring the relative levels of enzyme activity between two samples or more may be used as an indirect measure of the relative amount of total enzyme present within the different samples. Related to this, the present method may be first carried out in respect of a series of test samples containing known quantities of enzyme. The results obtained may be used to generate a standard curve, or a look up table, of enzyme activity plotted against enzyme concentration. A further test sample containing an unknown quantity of enzyme may thereafter be tested for enzyme activity and, based on data available from the standard curve or look up table, the absolute amount of enzyme within the test sample may be determined.

In a further application of the current method, a comparison of the relative enzyme activity between two samples, for example a control sample and an experimental sample, may be used to assess the effect of a potential modulator, for example an inhibitor, on enzyme activity. The invention will be further understood with reference to the following clauses:

1. An enzyme detection device for detecting the presence in a test sample of cleavage activity of an enzyme capable of cleaving a substrate, the device comprising:
   (i) an indicator molecule for adding to the test sample, said indicator molecule comprising
      (a) a cleavage site, which can be cleaved by said enzyme if said enzyme cleavage activity is present;
      (b) a first capture site; and
      (c) a detection region comprising a second capture site,
   wherein cleavage of the cleavage site results in release of a fragment of the indicator molecule comprising the detection region;
   (ii) a first capture zone to receive the test sample, wherein the first capture zone comprises first capture molecules capable of binding to the first capture site of the indicator molecule but not the cleaved fragment of the indicator molecule comprising the detection region and wherein the indicator molecule is captured by binding of the first capture site to the first capture molecules thereby substantially preventing any subsequent cleavage of the cleavage site by the enzyme; and
   (iii) a second capture zone to receive the test sample following contact of the test sample with the first capture zone, wherein the second capture zone comprises second capture molecules capable of binding to the second capture site of the indicator molecule, wherein the second capture zone is spatially separated from the first capture zone, and wherein detection of any cleaved indicator molecule via the detection region and bound via the second capture site to the second capture molecules, indicates the presence of cleavage activity of the enzyme in the test sample.
2. The device of clause 1 wherein the cleavage site is located within a substrate region of the indicator molecule, and said substrate region comprises a peptide, a protein, a carbohydrate, a lipid or a nucleic acid.
3. The device of clause 2 wherein the first capture site is contained within the substrate region.
4. The device of any of clauses 1-3 wherein the enzyme to be detected is selected from the following categories:— oxidoreductases, hydrolases and lyases, and include the subcategories of protease, peptidase, lipase, nuclease, carbohydrase, phosphatase, sulphatase, neuraminidase, esterase, DNAse, and RNAse.
5. The device of any of clauses 1-4 wherein the enzyme to be detected is a matrix metalloprotease or human neutrophil-derived elastase.
6. The device of any of clauses 1 to 5 wherein the indicator molecule comprises multiple cleavage sites and wherein cleavage at any one of the cleavage sites results in release of a fragment of the indicator molecule comprising the detection region.
7. The device of clause 6 wherein cleavage sites recognised by different enzymes capable of cleaving a substrate are incorporated into the indicator molecule.
8. The device of any of clauses 1-7 wherein the first capture site of the indicator molecule binds directly to the first capture molecule present in the first capture zone of the device.
9. The device of clause 8 wherein the first capture site of the indicator molecule and the first capture molecule present in the first capture zone of the device are two halves of a binding pair wherein the binding pair is selected from the following:—an antigen and an antibody or antigen binding fragment thereof; biotin and avidin, streptavidin, neutravidin or captavidin; an immunoglobulin (or appropriate domain thereof) and protein A or G; a carbohydrate and a lectin; complementary nucleotide sequences; a ligand and a receptor molecule; a hormone and hormone binding protein; an enzyme cofactor and an enzyme; an enzyme inhibitor and an enzyme; a cellulose binding domain and cellulose fibres; immobilised aminophenyl boronic acid and cis-diol bearing molecules; and xyloglucan and cellulose fibres and analogues, derivatives and fragments thereof.
10. The device of clause 9 wherein the binding pair is biotin and streptavidin.
11. The device of clause 9 wherein the first capture site of the indicator molecule comprises an epitope and the first capture molecule comprises an antibody which specifically binds to said epitope.
12. The device of any of clauses 1-6 wherein binding of the first capture site of the indicator molecule to the first capture molecule is indirect and mediated by an adaptor capable of simultaneously binding the first capture site and the first capture molecule.
13. The device of any of clauses 1-12 wherein a plurality of indicator molecules may bind to each first capture molecule.
14. The device of any of clauses 1-13 wherein the second capture site of the indicator molecule binds directly to the second capture molecule present in the second capture zone of the device.
15. The device of clause 14 wherein the second capture site and second capture molecules are two halves of a binding pair wherein the binding pair is selected from the following:—an antigen and an antibody or antigen binding fragment thereof; biotin and avidin, streptavidin, neutravidin or captavidin; an immunoglobulin (or appropriate domain thereof) and protein A or G; a carbohydrate and a lectin; complementary nucleotide sequences; a ligand and a receptor molecule; a hormone and hormone binding protein; an enzyme cofactor and an enzyme; an enzyme inhibitor and an enzyme; a cellulose binding domain and cellulose fibres; immobilised aminophenyl boronic acid and cis-diol bearing molecules; and xyloglucan and cellulose fibres and analogues, derivatives and fragments thereof.

16. The device of clause 15 wherein the binding pair is biotin and streptavidin.
17. The device of clause 15 wherein the second capture site of the indicator molecule comprises an epitope distinct from the epitope of the first capture site, and the second capture molecule comprises an antibody or antigen binding fragment thereof which specifically binds to said epitope.
18. The device of any of clauses 1-17 wherein the detection region of the indicator molecule comprises a reporter moiety.
19. The device of clause 18 wherein the reporter moiety is selected from the following: a gold particle; a chromogen; a luminescent compound; a fluorescent molecule; a radioactive compound; a visible compound; a liposome or other vesicle containing signal producing substances; an electroactive species; or a combination of enzyme and its substrate.
20. The device of clause 18 wherein the reporter moiety is a gold particle.
21. The device of any of clauses 1-17 additionally comprising a reporter molecule bound or capable of binding to the detection region of the indicator molecule.
22. The device of clause 21 wherein the detection region of the indicator molecule comprises a detection site, distinct and spatially separated from the second capture site, and the reporter molecule(s) bind(s) to the detection region via the detection site.
23. The device of clause 22 wherein the detection site comprises an epitope, distinct from any epitope present within the first capture site and second capture site, and the reporter molecule comprises an antibody which specifically binds to said epitope.
24. The device of clause 21 wherein the reporter molecule binds to the detection region via the second capture site, wherein binding of the reporter molecule to the second capture site does not impair the ability of the second capture site to bind second capture molecules.
25. The device of any of clauses 21-24 wherein the reporter molecule comprises a reporter moiety selected from the following: a gold particle; a chromogen; a luminescent compound; a fluorescent molecule; a radioactive compound; a visible compound; a liposome or other vesicle containing signal producing substances; an electroactive species; or a combination of enzyme and its substrate.
26. The device of any of clauses 21-25 wherein binding of the reporter molecule to the detection region is indirect and mediated by an adaptor capable of simultaneously binding the detection region and the reporter molecule.
27. The device of clause 26 wherein the adaptor is pre-complexed with the detection region prior to the addition of the test sample to the indicator molecule.
28. The device of clause 26 or 27 wherein the adaptor is streptavidin and the detection region comprises biotin.
29. The device of clause 26 or 27 wherein the adaptor is an adaptor binding pair, said binding pair comprising:
(i) a first member capable of binding to the detection region of the indicator molecule; and
(ii) a second member capable of binding to the first member of the pair and to the reporter molecule.
30. The device of clause 29 wherein the detection region of the indicator molecule comprises biotin, the first member of the adaptor binding pair is avidin or streptavidin, the second member of the adaptor binding pair is biotin, and the reporter molecule comprises a moiety capable of binding biotin.
31. The device of any of clauses 21-30 wherein multiple reporter molecules may bind to each indicator molecule.
32. The device of any of clauses 26-31 wherein the adaptor binds to the second capture site within the detection region of the indicator molecule such that the second capture site is bound indirectly by the second capture molecule present in the second capture zone of the device via the adaptor.
33. The device of clause 32 wherein the adaptor is streptavidin and the second capture molecule is biotin.
34. The device of any of clauses 1-33 wherein the device is a flow device, and the first capture zone and second capture zone are present at sequential locations along a chromatographic medium.
35. An indicator molecule for use in an enzyme detection device as defined by any one of clauses 1-34.
36. An indicator molecule for use in detecting the presence in a test sample of cleavage activity of an enzyme capable of cleaving a substrate, the indicator molecule comprising:
(a) a cleavage site, which can be cleaved by said enzyme if said enzyme cleavage activity is present;
(b) a first capture site; and
(c) a detection region comprising a second capture site, wherein cleavage of the cleavage site results in release of a fragment of the indicator molecule comprising the detection region.
37. The indicator molecule of clause 36 wherein the first capture site comprises one half of a binding pair and may be used to immobilise the indicator molecule and/or a fragment thereof comprising the first capture site at a site comprising the second half of the binding pair.
38. The indicator molecule of clause 37 wherein the binding pair is selected from the following:—an antigen and an antibody or antigen binding fragment thereof; biotin and avidin, streptavidin, neutravidin or captavidin; an immunoglobulin (or appropriate domain thereof) and protein A or G; a carbohydrate and a lectin; complementary nucleotide sequences; a ligand and a receptor molecule; a hormone and hormone binding protein; an enzyme cofactor and an enzyme; an enzyme inhibitor and an enzyme; a cellulose binding domain and cellulose fibres; immobilised aminophenyl boronic acid and cis-diol bearing molecules; and xyloglucan and cellulose fibres and analogues, derivatives and fragments thereof.
39. The indicator molecule of clause 37 wherein the binding pair is biotin and streptavidin.
40. The indicator molecule of clause 37 wherein the first capture site of the indicator molecule comprises an epitope capable of being recognised by an antibody or derivative thereof.
41. The indicator molecule of any one of clauses 37-40 wherein the second capture site comprises one half of a binding pair and may be used to immobilise the indicator molecule and/or a fragment thereof comprising the second capture site at a site comprising the second half of the binding pair.
42. The indicator molecule of clause 41 wherein the binding pair is selected from the following:—an antigen and an antibody or antigen binding fragment thereof; biotin and avidin, streptavidin, neutravidin or captavidin; an immunoglobulin (or appropriate domain thereof) and protein A or G; a carbohydrate and a lectin; complementary nucleotide sequences; a ligand and a receptor molecule; a hormone and hormone binding protein; an enzyme cofactor and an enzyme; an enzyme inhibitor and an enzyme; a cellulose binding domain and cellulose fibres; immobilised aminophenyl boronic acid and cis-diol bearing molecules; and xyloglucan and cellulose fibres and analogues, derivatives and fragments thereof.

43. The indicator molecule of clause 41 wherein the binding pair is biotin and streptavidin.

44. The indicator molecule of clause 41 wherein the second capture site of the indicator molecule comprises an epitope capable of being recognised by an antibody or derivative thereof.

45. A method for detecting the presence in a test sample of an enzyme capable of cleaving a substrate, the method comprising the steps of:
(i) providing an enzyme detection device comprising an indicator molecule for adding to the test sample, said indicator molecule comprising
   (a) a cleavage site, which can be cleaved by said enzyme if said enzyme cleavage activity is present;
   (b) a first capture site; and
   (c) a detection region comprising a second capture site, wherein cleavage of the cleavage site results in release of a fragment of the indicator molecule comprising the detection region;
a first capture zone to receive the test sample, wherein the first capture zone comprises first capture molecules capable of binding to the first capture site of the indicator molecule but not the cleaved fragment of the indicator molecule comprising the detection region; and
a second capture zone to receive the test sample following contact of the test sample with the first capture zone, wherein the second capture zone comprises second capture molecules capable of binding to the second capture site of the indicator molecule and wherein the second capture zone is spatially separated from the first capture zone;
(ii) providing a test sample;
(iii) adding the indicator molecules of the device to the test sample under conditions in which the enzyme, if present, can cleave the substrate region;
(iv) bringing the test sample into contact with the first capture molecules of the device such that any intact indicator molecules, if present, are bound to the first capture molecules within the first capture zone and wherein binding of the indicator molecules to the first capture molecules substantially prevents any subsequent cleavage of the cleavage site of the indicator molecule by the enzyme;
(v) bringing the test sample into contact with the second capture molecules of the device such that any fragments of cleaved indicator molecule comprising the detection region are bound, via the second capture site, by the second capture molecules; and
(vi) detecting the presence or absence or level of fragments of cleaved indicator molecule comprising the detection region in the second capture zone via the detection region in order to determine the presence of enzyme in the test sample.

46. The method of clause 45 wherein the enzyme detection device is as defined in any of clauses 1-33.

47. The method of clause 45 or 46 wherein detection of the intact indicator molecule, or cleaved fragment thereof present in the second capture zone, is carried out by the detection of a reporter moiety present within the detection region.

48. The method of clause 45 or 46 wherein detection of the intact indicator molecule, or cleaved fragment thereof present in the second capture zone, is carried out by the addition of a reporter molecule capable of binding to the detection region.

49. The method of clause 48 wherein the reporter molecule is added to the indicator molecule prior to the addition of the test sample.

50. The method of clause 48 wherein the reporter molecule is added to the indicator molecule in the first capture zone of the device.

51. The method of any of clauses 45-50 wherein the presence of reporter molecules bound to cleaved fragments of indicator molecules located within the second capture zone indicates that an enzyme capable of cleaving the cleavage site of the indicator molecule is present within the test sample.

52. The method of any of clauses 45-50 wherein the presence of reporter molecules in the first capture zone but not in the second capture zone indicates that no enzyme is present in the test sample.

53. A method of determining the amount of an enzyme capable of cleaving a substrate in a first sample relative to the amount of said enzyme in one or more additional samples comprising the steps of:
(i) providing an enzyme detection device comprising an indicator molecule for adding to the test sample, said indicator molecule comprising
   (a) a cleavage site, which can be cleaved by said enzyme if said enzyme cleavage activity is present;
   (b) a first capture site; and
   (c) a detection region comprising a second capture site, wherein cleavage of the cleavage site results in release of a fragment of the indicator molecule comprising the detection region;
a first capture zone to receive the test sample, wherein the first capture zone comprises first capture molecules capable of binding to the first capture site of the indicator molecule but not the cleaved fragment of the indicator molecule comprising the detection region; and
a second capture zone to receive the test sample following contact of the test sample with the first capture zone, wherein the second capture zone comprises second capture molecules capable of binding to the second capture site of the indicator molecule
and wherein the second capture zone is spatially separated from the first capture zone;
(ii) providing a first sample;
(iii) adding the indicator molecules of the device to the first sample under conditions in which the enzyme, if present, can cleave the cleavage site;
(iv) bringing the first sample into contact with the first capture molecules of the device such that any intact indicator molecules, if present, are bound to the first capture molecules within the first capture zone and wherein binding of the indicator molecules to the first capture molecules substantially prevents any subsequent cleavage of the cleavage site of the indicator molecule by the enzyme;
(v) bringing the first sample into contact with the second capture molecules of the device such that any fragments of cleaved indicator molecule comprising the detection region are bound, via the second capture site, by the second capture molecules;
(vi) detecting the presence and level of intact indicator molecule in the first capture zone and the presence and level of cleaved indicator molecule in the second capture zone;

(vii) repeating steps (i) to (vi) for the one or more additional samples;
(viii) comparing the levels obtained for the first and one or more additional samples in order to determine the relative levels of enzyme present in each sample.
54. The method of clause 53 wherein the enzyme detection device is as defined in any of clauses 1-34.
55. The method of clause 53 or 54 wherein detection of the intact indicator molecule in the first capture zone and/or cleaved indicator molecule present in the second capture zone, is carried out by the detection of a reporter moiety present within the detection region.
56. The method of clause 53 or 54 wherein detection of the intact indicator molecule in the first capture zone and/or cleaved indicator molecule present in the second capture zone, is carried out by the addition of a reporter molecule capable of binding to the detection region.
57. The method of any one of clauses 53-56 wherein at least one of the samples used for comparison comprises a known amount of enzyme.
58. Use of an enzyme detection device as defined in any of clauses 1-34 for detecting the presence in a test sample of an enzyme capable of cleaving a substrate.
59. An enzyme detection device substantially as herein described with reference to the accompanying drawings
60. A method for detecting the presence in a test sample of an enzyme capable of cleaving a substrate substantially as herein described with reference to the accompanying drawings.
61. A method for determining the amount of an enzyme capable of cleaving a substrate in a first sample relative to the amount of said enzyme in one or more additional samples substantially as herein described with reference to the accompanying drawings.
62. Use of an enzyme detection device substantially as herein described with reference to the accompanying drawings.

BRIEF DESCRIPTION OF THE DRAWINGS

The invention will now be described by way of example with respect to the accompanying drawings in which.

DESCRIPTION OF PREFERRED EMBODIMENTS

Figure 1:
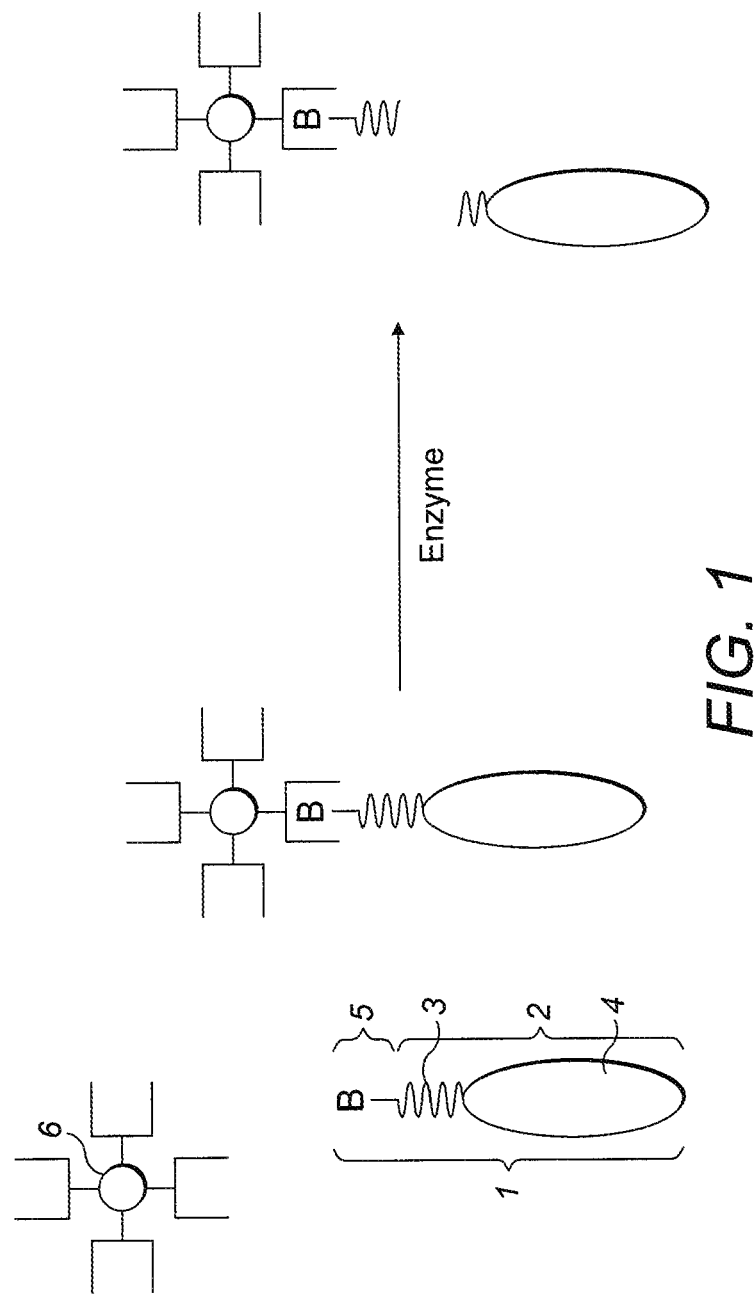
FIG. 1 is a schematic view of an indicator molecule in accordance with one embodiment of the present invention.
Figure 2:
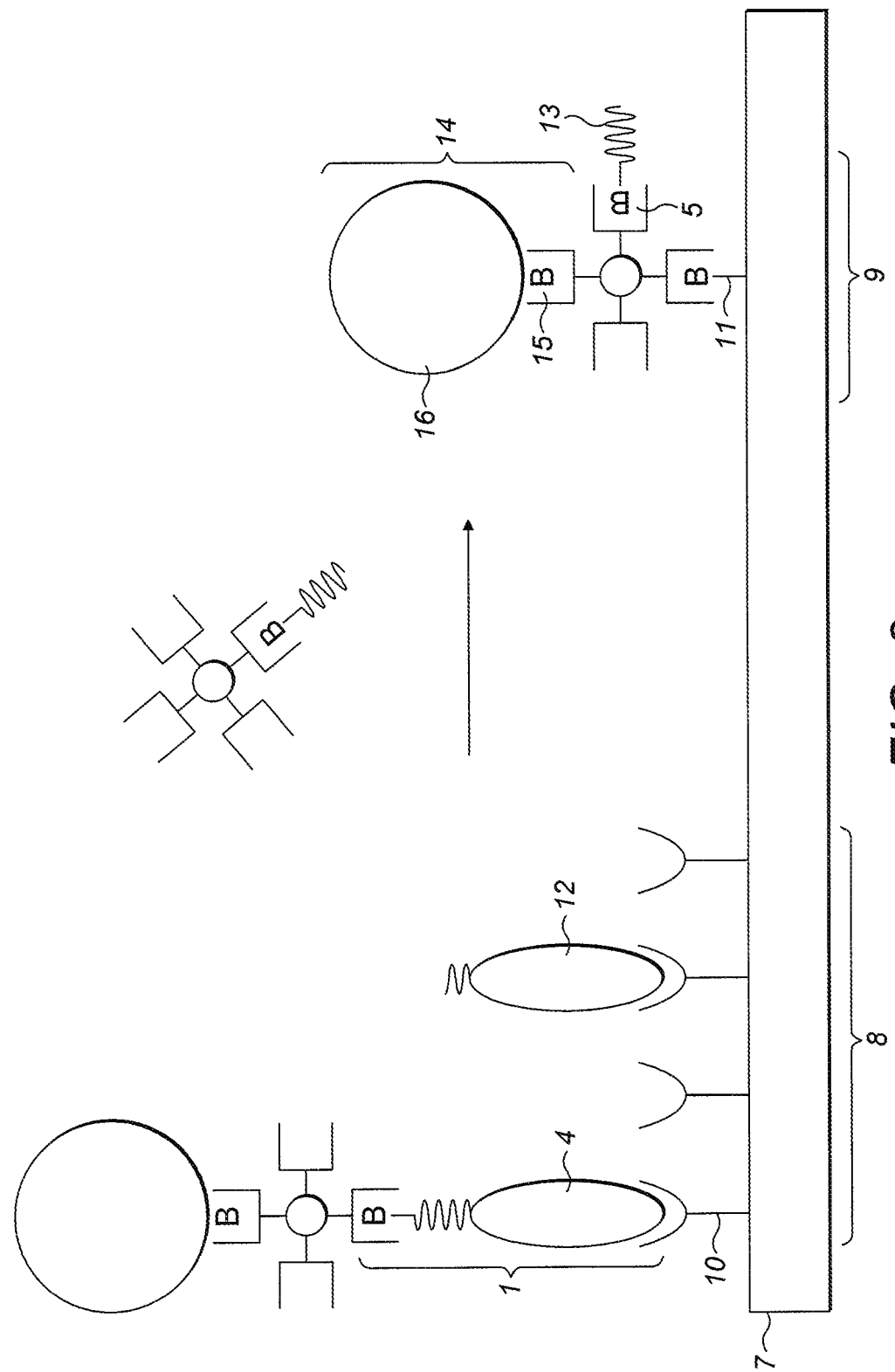
FIG. 2 is a schematic view of an enzyme detection device in accordance with one embodiment of the present invention incorporating the indicator molecule of FIG. 1.

FIG. 1 shows an indicator molecule according to a preferred embodiment of the present invention. The indicator molecule (1) as shown comprises a substrate region (2) containing a single cleavage site (3) and a first capture site (4). In addition, the indicator molecule (1) has a detection region (5) comprising a second capture site. In the embodiment shown, the detection region (5) consists of a biotin moiety (B) and is therefore capable of binding to a multivalent streptavidin adaptor molecule (6). The indicator molecule (1) may be pre-complexed with the adaptor molecule (6) prior to exposure to the test sample suspected to contain the enzyme (as shown). Alternatively, the adaptor molecule may be added to the indicator molecule (1) after enzyme cleavage has occurred.
Once the indicator molecule (1) of the invention is added to a test sample, any enzyme specifically recognising the cleavage site (3) present, may cleave the indicator molecule (1) resulting in dissociation of the first capture site (4) and the detection region (5) of the molecule.
FIG. 2 shows an enzyme detection device according to a preferred embodiment of the present invention. The device comprises an indicator molecule (1) as defined in FIG. 1, and a chromatographic test strip (7) comprising an upstream first capture zone (8) and a downstream second capture zone (9).
In the embodiment of the device shown, the first capture zone (8) is defined by the presence of first capture molecules (10) immobilized by binding to the solid support of the test strip (7). The second capture zone (9) is defined by the presence of second capture molecules (11) and is spatially separated from the first capture zone (8) by virtue of immobilization of the second capture molecules (11) at a discrete downstream location along the long axis of the chromatographic test strip (7).
In use, the indicator molecule (1) is added to the test sample prior to bringing the test sample into contact with the first capture zone (8) of the device. As shown in FIG. 2, the indicator molecule, once present in the first capture zone (8) of the device, binds to the first capture molecules (10) present therein via the first capture site (4). This binding may be direct (as shown) or indirect, but in either case, substantially prevents any subsequent cleavage of the cleavage site by any enzyme in the test sample. In preferred embodiments of the present device, the first capture molecules (10) will typically exhibit high binding affinity for the indicator molecule (1), and in particular, an affinity that is greater than the affinity of the enzyme for the indicator molecule (1). As such, once the indicator molecule (1) within the test sample is brought into contact with the first capture molecules, there will be essentially no further cleavage of indicator molecules (1) by the enzyme.

The first capture molecules (10) will bind any intact indicator molecule (1) and may bind any cleaved fragments of indicator molecule containing the first capture site (12). However, in certain embodiments, cleavage at the cleavage site may disrupt the first capture site such that the residual fragments of indicator molecule not containing the detection region do not bind to the first capture molecules within the first capture zone.

In the preferred embodiment shown, the device is configured as a lateral flow device comprising a chromatographic test strip (7). In this embodiment, the test sample is typically applied to the test strip at a location upstream from the first capture zone and is thereafter drawn, by capillary action, along the test strip in the direction indicated by the arrow. Thus, any fragments of cleaved indicator molecule not captured at the first capture zone (8) will proceed into the second capture zone (9).

In the second capture zone (9) of the device, cleaved indicator molecule fragments comprising the detection region (13) are localised by virtue of the binding interaction between the second capture site (B) present within the detection region (5) and the second capture molecules (11) present within the second capture zone (9).

In the embodiment of the device shown in FIG. 2, the detection region of the indicator molecule comprises a biotin moiety (B) and is bound by a multivalent streptavidin adaptor molecule (6). This streptavidin adaptor (6) acts as a bridge between the detection region (5) of the indicator molecule and the second capture molecule, which also comprises a biotin moiety (11).

In the methods of the present invention, detection of bound indicator molecule or a cleaved fragment thereof may be performed at both capture zones or only at one or other of the capture zones, typically the second capture zone. Detection may be carried out by measuring the signal generated either by a reporter moiety already present within the detection region, or by measuring the signal generated by a reporter molecule bound specifically to the detection region.

In FIG. 2, a reporter molecule (14) is shown bound via a streptavidin adaptor molecule (6) to the detection region of the indicator molecule. The reporter molecule itself comprises a biotin moiety (15), which mediates binding to the streptavidin adaptor, and a gold particle (16) conjugated to said biotin moiety. Alternative means of coupling a reporter molecule to the detection region of the indicator molecule are described in detail above.

In the embodiment shown, the streptavidin adaptor molecule (6) bound to the detection region of the indicator molecule (5) serves a dual purpose at the second capture zone in that it mediates binding of the indicator molecule (1) to both the second capture molecule (11) and the reporter molecule (14) via their respective biotin moieties.

Figure 3:
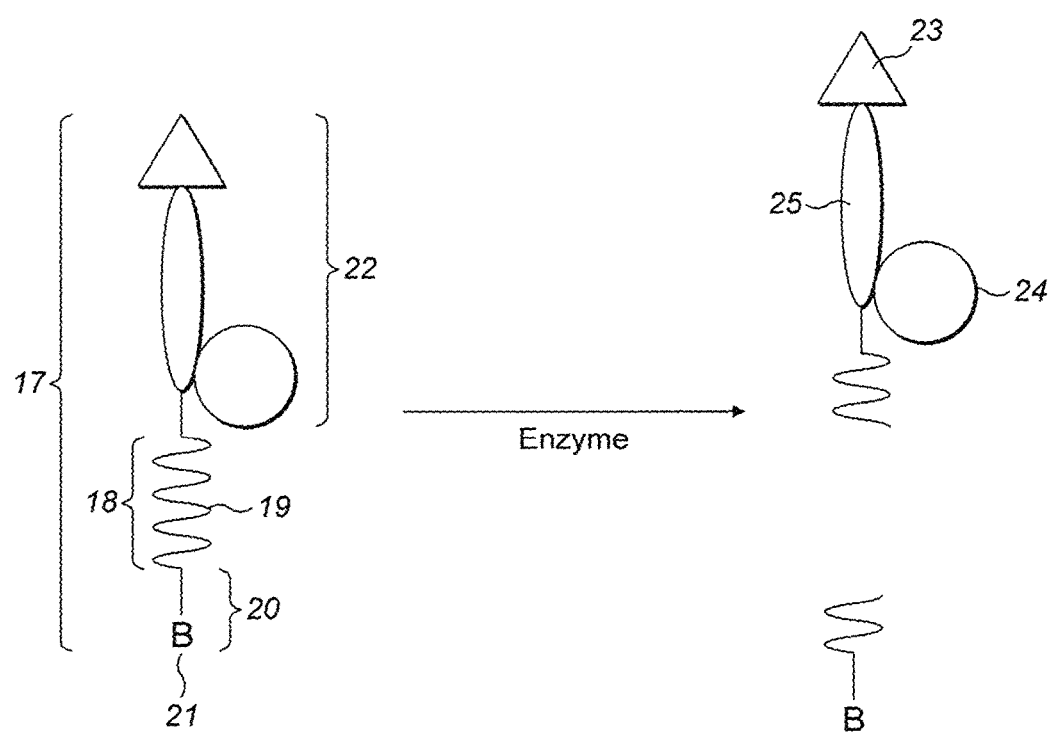
FIG. 3 is a schematic view of an indicator molecule in accordance with a second embodiment of the present invention.

FIG. 3 shows an indicator molecule according to a second preferred embodiment of the present invention. The indicator molecule (17) as shown comprises a substrate region (18) containing a single cleavage site (19) and a separate first capture region (20) containing a first capture site (21). In addition, the indicator molecule has a detection region (22) comprising a detection site (23) and a separate second capture site (24) distanced from the detection site by virtue of a linker (25).

In accordance with all other embodiments of the invention, once the indicator molecule of the invention is added to a test sample, any enzyme specifically recognising the cleavage site present, may cleave the indicator molecule resulting in dissociation of the first capture site (21) and the detection region (22) of the molecule.

Figure 4:
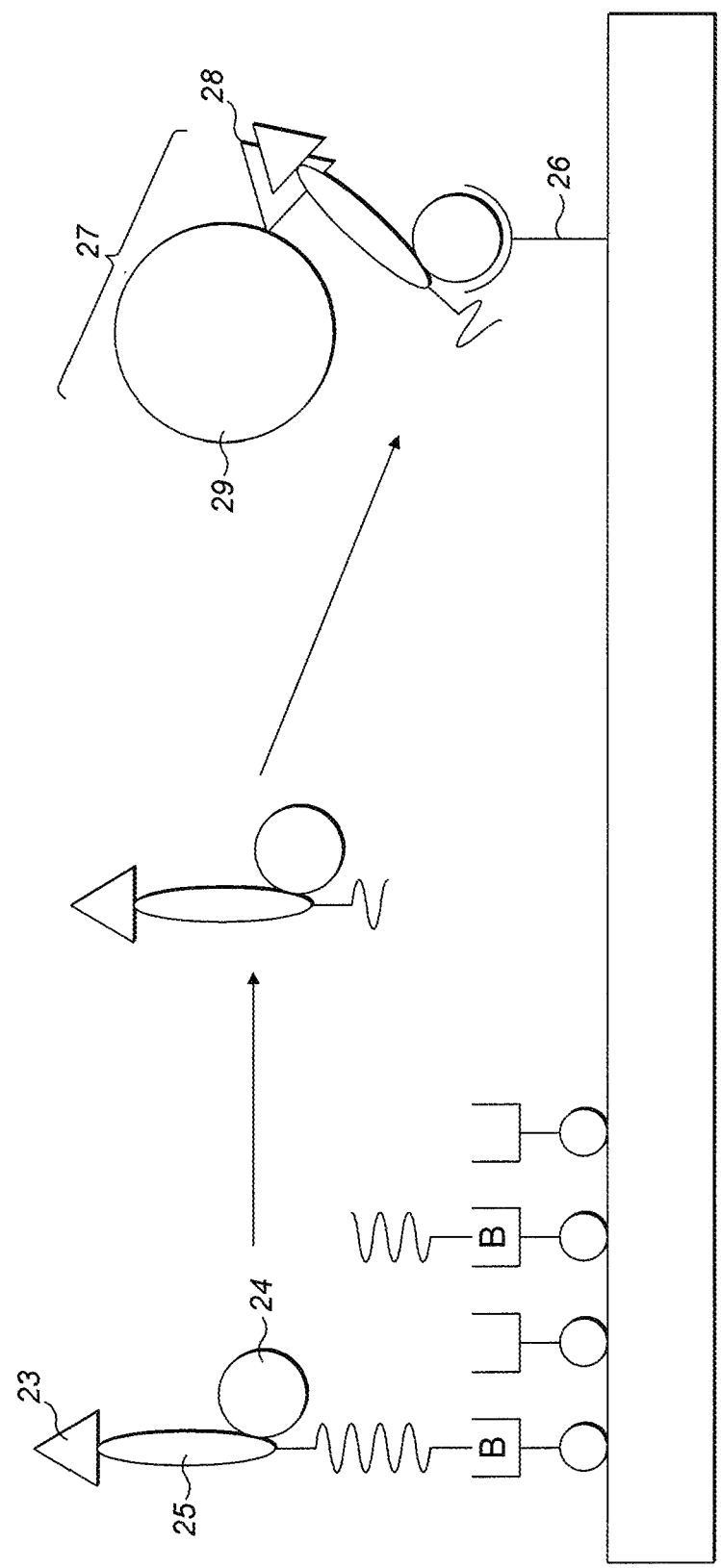
FIG. 4 is a schematic view of an enzyme detection device in accordance with a second embodiment of the present invention incorporating the indicator molecule of FIG. 3.

FIG. 4 shows an enzyme detection device similar to the device represented in FIG. 2 but incorporating the indicator molecule of FIG. 3. In this second preferred embodiment of the device, the main difference lies in the detection region of the indicator molecule, which in contrast to the single entity shown in FIGS. 1 and 2, comprises three distinct entities: a second capture site (24), a distinct detection site (23) and a linker separating the two sites (25). In this configuration, the second capture site (24) is preferably an epitope and the second capture molecule (26) comprises an antibody which specifically binds to said epitope. Moreover, the detection site (23) is preferably a distinct epitope and the reporter molecule (27) comprises an antibody (28) which specifically binds to this distinct epitope. In the embodiment of FIG. 4, the antibody of the reporter molecule is shown conjugated to a gold particle (29) for the purposes of detection.

Figure 5:
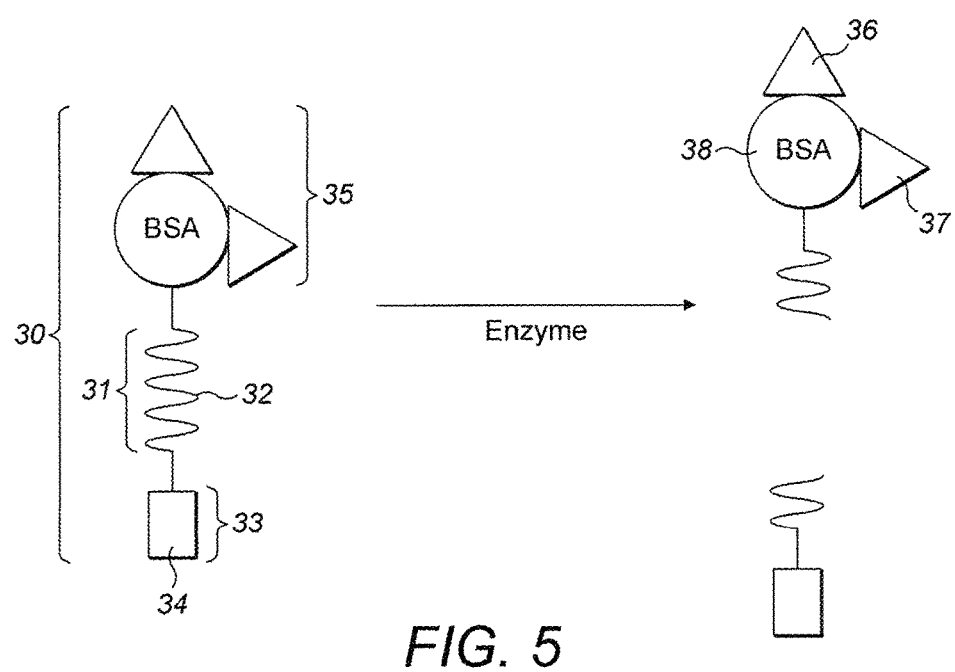
FIG. 5 is a schematic view of an indicator molecule in accordance with a third embodiment of the present invention.

FIG. 5 shows an indicator molecule according to a third preferred embodiment of the present invention. The indicator molecule as shown (30) comprises a substrate region (31) containing a single cleavage site (32) and a first capture region (33) comprising a first capture site (34). In addition, the indicator molecule has a detection region (35) comprising a detection site (36) and a second capture site (37) separated from the detection site by virtue of a BSA moiety (38).

In accordance with all other embodiments of the invention, once the indicator molecule of the invention is added to a test sample, any enzyme specifically recognising the cleavage site present, may cleave the indicator molecule resulting in dissociation of the first capture site (34) and the detection region (35) of the molecule.

Figure 6:
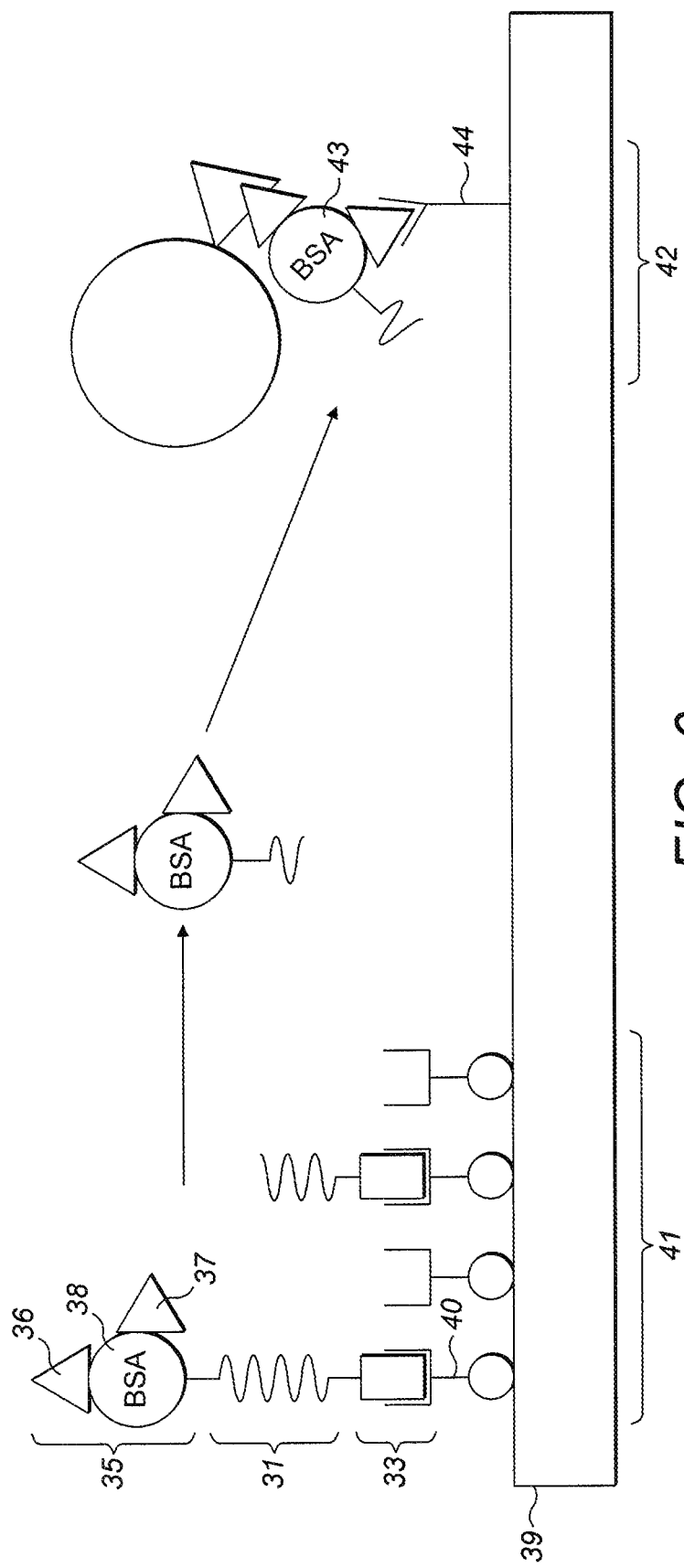
FIG. 6 is a schematic view of an enzyme detection device in accordance with a third embodiment of the present invention incorporating the indicator molecule of FIG. 5.

FIG. 6 shows an enzyme detection device similar to the devices represented in FIGS. 2 and 4 but incorporating the indicator molecule of FIG. 5. In this third preferred embodiment of the device, the first capture region (33), substrate region (31) and detection region (35) are distinct entities, and within the detection region, there is a distinct detection site (36) and second capture site (37). In the embodiment shown, the two sites of the detection region are separated by a BSA carrier (38) and the two sites are identical. In accordance with the embodiments of the device shown in FIGS. 2 and 4, the device is configured as a lateral flow device comprising a chromatographic test strip (39). In this embodiment, the test sample is typically applied to the test strip at a location upstream from the first capture zone and is thereafter drawn, by capillary action, along the test strip in the direction indicated by the arrow. Thus, any fragments of cleaved indicator molecule not captured by first capture molecules (40) at the first capture zone (41) will proceed into the second capture zone (42).

In the second capture zone (42) of the device, cleaved indicator molecule fragments comprising the detection region (43) are localised by virtue of the binding interaction between the second capture site (37) present within the detection region (35) and the second capture molecules (44) present within the second capture zone (42).

The invention will be further understood with reference to the following experimental examples.

EXAMPLES

Example 1

A Reverse ELTABA Platform Utilizing a Dual Peptide Albumin Conjugate Indicator Molecule for Detection of Matrix Metalloprotease-8 (MMP-8)

The indicator molecule consists of a BSA molecule acting as a carrier protein onto which is attached two peptides, one of which contains the cleavage site and a first capture region, the second contains a detection region and a second capture region. Multiple peptides are attached to the BSA molecule, with a higher ratio of the second peptide to the first.

A kit comprises the following components:—

1) A device for sample collection (e.g. for urine)
2) A chase buffer for re-hydrating the gold conjugate consisting of Tris buffer saline (TBS) at pH 8.0 and 1% TWEEN™20 (Polyoxyethylene (20) sorbitan monolaurate).
4) A gold conjugate in a liquid form that consists of gold particles adhered to sheep antibodies which recognise the second capture region.
4) A lateral flow test-strip. The test strip has a hidden capture zone comprising a sheep antibody in the form of three pre-absorbent lines (PA lines) to the first capture region and a second capture zone which comprises a second sheep antibody to the second capture region as a first test line across the flow-path of the test strip.
5) A microtitre plate in which the sample may be placed, together with the indicator molecule.
6) An indicator molecule. The indicator molecule consists of a peptide containing a sequence of amino acids biased for MMP-8. The sequence GPQGIFGQ (SEQ ID NO:1) is especially suitable, but many others are available and these can be derived from the scientific literature. The peptide carries a cysteine group on the N terminus allowing it be conjugated to a BSA carrier protein using standard maleimide based chemistry. The peptide contains a capture region that is recognised by the sheep antibodies which are immobilised in the hidden capture zone. A second peptide is additionally conjugated to the BSA carrier protein using the same chemistry; this peptide is recognised by the sheep antibody which is immobilised in the test line capture zone and to the gold reporter particles.

A. Manufacture of the Dual Peptide Albumin Conjugate.
1. 5 mg of Bovine Serum Albumin (BSA) (VWR, 44155J) was dissolved in 2.375 ml Phosphate buffer saline (PBS) pH7.4.
2. 125 μl of 2 mg/ml SMCC (Thermo Scientific, M-6035) in Dimethyl sulfoxide (sigma, 154938) was added to the solution of BSA in PBS.
3. The reaction mixture was incubated for 30 minutes at room temperature.
4. A PD-10 column (GE Healthcare, 17-0851-01) was equilibrated with 40 ml PBS+1 mM EDTA.
5. After incubation the sample (2.5 ml) was loaded into the column.
6. The Column was flushed with 3.5 ml PBS/EDTA to elute the activated BSA.
7. Required amounts of the two peptides were added and incubated for 2 hours.

|  | 3:1 ratio |
|---|---|
| MOL120 | 0.8 mg |
| MOL038C | 0.5 mg |

8. The solution was dialysed in PBS overnight (30,000 MWCO dialysis tube) to facilitate the removal of excess peptide.

B. Manufacture of CF1058:40 nm Gold Conjugate
1. 18.51 μl of CF1058 1.35 mg/ml stock solution (Mologic, CF1058) was added to 181.5 μl of 20 mM TAPS Buffer pH8.5 to give the optimal concentration of 25 μg/ml antibody.
2. 1 ml 40 nm Gold OD5 (BBI, GC40) was added and the mixture was vortexed for 5-10 seconds.
3. The mixture was left to conjugate for 10 minutes on the bench at room temperature.
4. Finally, 12.51 μl of a 50 mg/ml solution of beta casein (Sigma, C6905) was added.

C. Preparation of Antibody-Impregnated Nitrocellulose Membrane.

All reagents were striped on CN140 membrane (Sartorius, CN140) with an Imagene Isoflow flat bed dispenser. PA lines comprised of 0.93 mg/ml sheep antibody CF1060 (Mologic, CF1060) at 4, 6 and 8 mm from base of membrane at a dispense rate of 0.41/mm. Test line sheep antibody CF1058 (Mologic, CF1058) was plotted at 1 mg/ml at a dispense rate of 0.1 μl/mm, 13 mm from the base of the membrane. Processed membrane was dried in an infra-red drying tunnel at 45° C. The dried antibody-impregnated Nitrocellulose Membrane was stored in a sealed foil pouch with desiccant at room temperature.

D. Manufacture of Strips.
1. A 60×300 mm piece of clear plastic film with a release liner protected adhesive, serving as the back laminate, (G&L Precision Die Cutting, 48077) was placed on top of a worktable. The release liner was peeled to expose the adhesive side.
2. The reaction membrane, prepared as in section C, was attached on top of the adhesive side of the back cover lined up with the lower edge of the backing card.

Absorbent pad was attached on to the backing card, creating a 2 mm overlap over the NC.

The laminated card was cut into 4 mm strips using the Biodot cutter and was subsequently stored in foil pouch with desiccant.

E. Running Buffer
Aq. Solution of 50 mM Tris, 150 mM sodium chloride, 20 mM sodium azide, 1% vol/vol TWEEN™20 (Polyoxyethylene (20) sorbitan monolaurate), at pH 8.0.

F. Wet Assay Running Procedure:
1. MMP-8 catalytic domain (ENZO life science, BML-SE-255) was serially diluted 1 in 2 from a starting concentration of 100μg/ml down to 0.78μg/ml in running buffer (20 μl volumes) in a microtitre plate.
2. 4 μl of a 20 μg/ml solution of the indicator molecule (diluted in TBST) was added to each 20 μl MMP-8 solution in the well.
3. Incubated for 10 minute at room temperature.
4. Strips were added to the wells, allowing the solutions to flow up the strips until the wells were empty.
5. Strips were transferred to a second well containing 20 μl OD1 gold conjugate (diluted in running buffer), and run to completion.
6. Strips were transferred to a 3$^{rd}$ set of wells with 20 μl running buffer and run to completion.

The test strip was added to a defined volume of liquid (the test sample) after the 10 minute incubation period. The indicator molecule which was added to the sample prior to the incubation period was able to bind to the sheep antibodies (CF1060) in the hidden capture zone via the $1^{st}$ capture region. Any MMP-8 present in the sample cleaved the indicator molecule at the cleavage site, allowing the release of the cleaved fragment from the hidden capture zone to bind to the test line antibody (CF1058). This complex was formed with the $2^{nd}$ capture region incorporated in the other peptide (MOL120) which was also attached to the BSA carrier protein.

Once the sample had travelled through the test strip aided by the absorbent pad that acted as a reservoir, the strip was introduced to the gold conjugate, CF1058:40 nm. As the conjugated gold particles entered the hidden capture zone, any intact indicator molecule bound to the PA lines which still contained the peptide MOL120 was labelled. Those fragments containing MOL120 that were released as a consequence of enzyme digestion were detected on the test line by the gold conjugate.

The lines that were formed were assessed by their relative intensities. The presence of a test line indicated that there was protease present in the test sample. A negative test line indicated a zero or low level of protease that was below the detectable limit. Stages in between these extremes indicated different levels of protease in the test sample. The intensity of the developed coloured lines was measured visually using a semi-quantitative scoring system with a scale of 0-10, in which 1 was the lowest detectable colour intensity and 10 was the highest observed colour intensity. The sensitivity in the above example when exposed to MMP-8 in a buffer system was approximately 12.5 µg/ml taking the background signal into account.

Figures 7A, 7B:
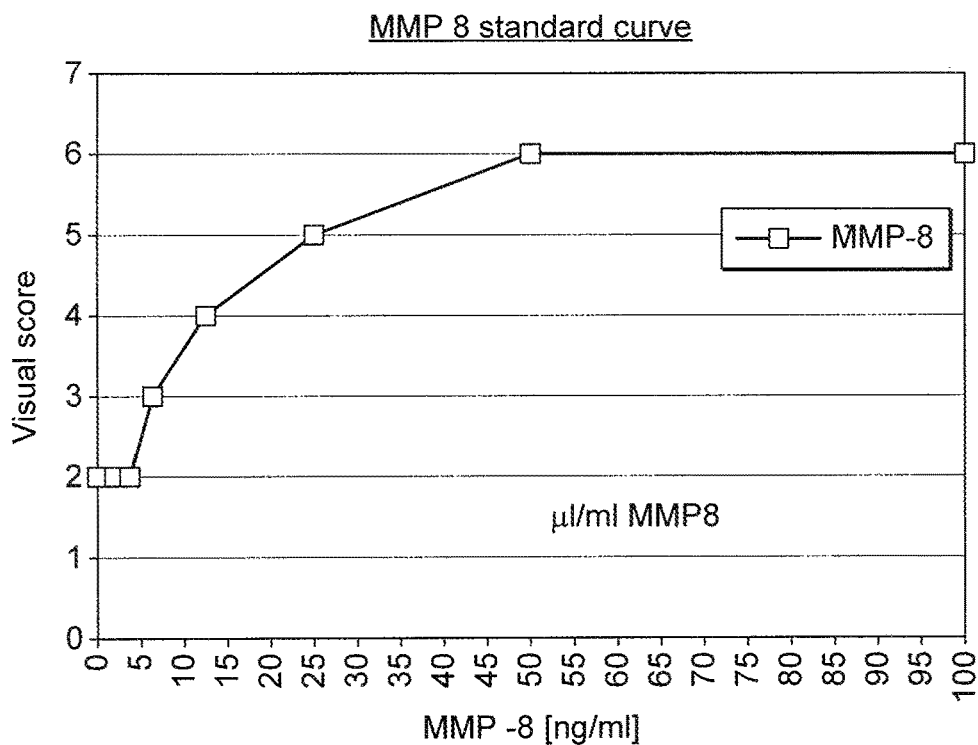
FIG. 7 shows results produced using an enzyme detection device according to the present invention to detect Matrix Metalloprotease-8 (MMP-8) activity.

FIG. 7 shows signals generated with a dilution curve of MMP-8 (1 being the lowest detectable signal and 10 being the highest).

Example 2

A Reverse ELTABA Platform Utilizing a Polystreptavidin: Peptide Complex Indicator Molecule for Detection of Matrix Metalloprotease-9 (MMP-9)

A kit comprises the following components:—
1) A device for sample collection (e.g. for urine)
2) A chase buffer for re-hydrating the gold conjugate consisting of Tris buffer saline (TBS) at pH 8.0 and 1% TWEEN™20 (Polyoxyethylene (20) sorbitan monolaurate).
3) A lateral flow test-strip, which is mounted in a plastic case. The test strip has a hidden capture zone which comprises of a sheep antibody in the form of four pre-absorbent lines (PA lines), a second capture zone which comprises biotin conjugated to a carrier protein as a first test line across the flow-path of the test strip and a third capture zone which comprises anti chicken antibodies adsorbed as a control line across the flow-path of the test strip, downstream of the test line. There is an observation window in the plastic case through which to view the test and control line. There is also an integrated sample receiving pad, upstream of the first test line. In addition, the test strip has gold particles bearing biotin dried into the test strip upstream of the sample-receiving pad which can be reconstituted by the addition of a buffer in a second well that receives the chase buffer upstream of the gold conjugate pad.
4) A tube, in which the sample collection device may be placed, together with the indicating molecule.
5) An indicator molecule, (which may be incorporated in the sample collection device). The indicator molecule consists of a peptide containing a sequence of amino acids biased for MMP-9. The sequence GPQGIFGQ (SEQ ID NO:1) is especially suitable, but many others are available and these can be derived from the scientific literature. The indicator molecule carries a terminal biotin group, connected via a polyethylene glycol spacer/linker which allows it to form a complex with the adapter molecule, polystreptavidin. Also incorporated is the $1^{st}$ capture region which is recognised by the sheep antibodies which are immobilised in the hidden capture zone.
6) An adapter molecule e.g. polystreptavidin that contains multiple binding regions that can form a complex with the indicator molecule that contains the cleavage site.

The Test Strip

A test strip for the detection of protease activity in a fluid sample was constructed in accordance with the present invention, as described below. The assay is based on the cleavage of the indicator molecule in the presence of MMP-9 to yield a fragment that will bind to the test line. Various samples were tested with the strip including wound fluid samples for the detection of protease activity.

A. Preparation of Gold-Impregnated Conjugate Pads

Whatman Glass fiber pad (Whatman, Rapid 24Q, 12 mm×300 mm) was sprayed with biotin:40 nm gold conjugate (Innova Bioscience) at OD4, and Chicken IgY Gold conjugate (Mologic) at OD2, diluted in gold drying buffer (50 mM Tris, 150 mM sodium chloride, 20 mM sodium Azide, 1% BSA, 10% Trehalose dihydrate, 1 % TWEEN™20 (Polyoxyethylene (20) sorbitan monolaurate) at pH 8.0) at 0.9 µl /mm with the Isoflow dispenser (7 mm spray height). Processed conjugate band was dried in a tunnel dryer at 60° C. at a speed of 5 mm/sec. The dried gold conjugate-impregnated conjugate pads were stored in a sealed foil pouch with desiccant at room temperature.

B. Preparation of Antibody-Impregnated Nitrocellulose Membrane

All reagents were striped on Millipore HF090 membrane (Millipore, HF09004S40, 40×300 mm) at a dispense rate of 0.05 µl/mm. PA lines comprised of 1 mg/ml CF1060 (Mologic) at 10, 12, 14 and 16 mm from base of membrane. Test line BSA biotin (Mologic) at a concentration of 0.4 mg/ml at 23 mm from base of membrane and control line Goat anti Chicken IgY (Lampire, 7455207) at a concentration of 0.5 mg/ml at 28 mm from base of membrane. Processed membrane was dried in a tunnel dryer at 60° C. at a speed of 10 mm/sec. The dried antibody-impregnated Nitrocellulose Membrane was stored in a sealed foil pouch with desiccant at room temperature.

C. Chase Buffer

Aq. Solution of 50 mM Tris, 150 mM sodium chloride, 20 mM sodium azide, 1% vol/vol TWEEN™20 (Polyoxyethylene (20) sorbitan monolaurate), at pH 8.0.

D. Card Assembly

Figure 8:
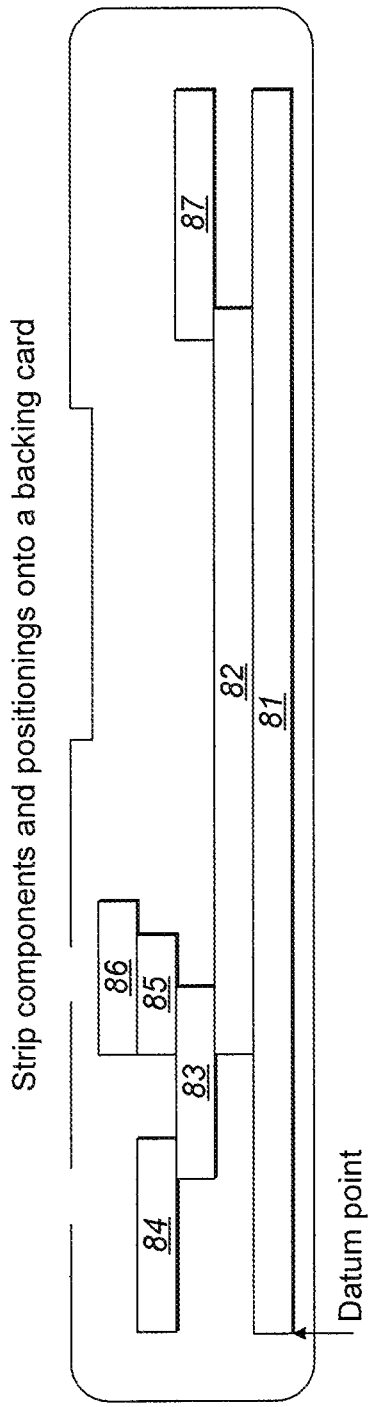
FIG. 8 shows a chromatographic test strip for use in conjunction with the enzyme detection device of the present invention.

A test card was assembled according to the following procedure and in accordance with FIG. 8, which specifies the exact longitudinal dimensions and position of each of the card components. Following preparation, the card was trimmed to obtain a plurality of strips for protease assay.

1. A 75×300 mm piece of clear plastic film with a release liner protected adhesive, serving as the back laminate

(81) (G&L Precision Die Cutting, 28840) was placed on top of a worktable. The release liner was peeled to expose the adhesive side of the tape.
2. The reaction membrane (82), prepared as in section B, was attached on top of the adhesive side of the back cover (81), 16 mm from the lower end.
3. The impregnated conjugate pad (83), prepared as in section A, was attached on top of the back cover (81) with 1 mm overlap on top of the reaction membrane (82).
4. The buffer pad (84, Whatman, CFS, 11×300 mm) was placed on top of the back cover (81) with 6 mm overlap on top of the conjugate pad (83).
5. The double sided tape (85, G&L Precision Die Cutting, GL-187) was attached over the conjugate pad (83) 15 mm from the lower end.
6. The sample receiving pad/blood separator membrane (86, Spectral SG membrane, Primecare) was placed over the tape (85) with cover removed, 15 mm from the lower end.
7. The absorbent pad (87, Gel blotting paper, Ahlstrom, grade 222, 23×300 mm) was placed on top of the upper side of the back cover (81) with a 3 mm overlap on top of the reaction membrane (82).

The card was trimmed to 4 mm width strips using an automated die cutter (Kinematic, 2360) and assembled into 2 well plastic housings (BBI Dundee, vision). The devices were closed using a pneumatic device clamp specifically manufactured for these devices at Mologic.

In the example described below, buffer standards were produced containing different concentrations of MMP-9 (Mologic) ranging from 2000 ng/ml down to 62.5 ng/ml.

STEP 1: A sample of fluid (the test sample) was placed in a collection device with a defined amount of peptide (6 ng/test). The collection device was rotated vigorously in order for the sample to mix sufficiently with the indicator molecule. This reaction mixture was incubated at ambient temperature for a defined period of time (e.g. 10 minutes) after which the adapter molecule (100 ng/test) was subsequently added which formed complexes with the biotin on the indicator molecule.

STEP 2: At the end of the incubation period, a defined volume of liquid was dropped onto the sample receiving pad (86). The indicator molecule which was added to the sample prior to the incubation period was able to bind to the sheep antibodies (CF1060) in the hidden capture zone via the $1^{st}$ capture region. Any MMP-9 present in the sample cleaved the indicator molecule at the cleavage site, allowing the release of the cleaved fragment from the hidden capture zone. The cleaved fragment migrated towards the biotin test line where it was immobilised via the polystreptavidin adapter molecule.

STEP 3: Once the sample had travelled through the test strip (82) aided by the absorbent pad (87) that acted as a reservoir, two drops of the chase buffer provided in the kit was added to a buffer pad (84) that made contact with and re-hydrated the dried biotin attached to the gold particles. As the conjugated gold particles entered the hidden capture zone any intact indicator molecule bound to the pre-absorbent lines was labelled via the polystreptavidin adaptor molecule. Those that had not bound to the intact indicator molecule in the hidden capture zone migrated down the strip and labelled any adaptor molecule captured by the test line. A separate control system was used that comprised chicken IgY attached to gold particles which bound to a Goat anti Chicken IgY control line. The presence of a line indicated that the test was complete.

The lines that were formed were assessed by their relative intensities. The presence of a test line and the presence of a full strength control line indicated that there was protease present in the test sample. A negative test line indicated a zero or low level of protease that was below the detectable limit. Stages in between these extremes indicated different levels of protease in the test sample. The intensity of the developed coloured lines was measured visually and with an NES Lateral flow device reader. A semi-quantitative scoring system with a scale of 0-10, in which 1 was the lowest detectable colour intensity and 10 was the highest observed colour intensity was used for the visual readings.

Figure 9:
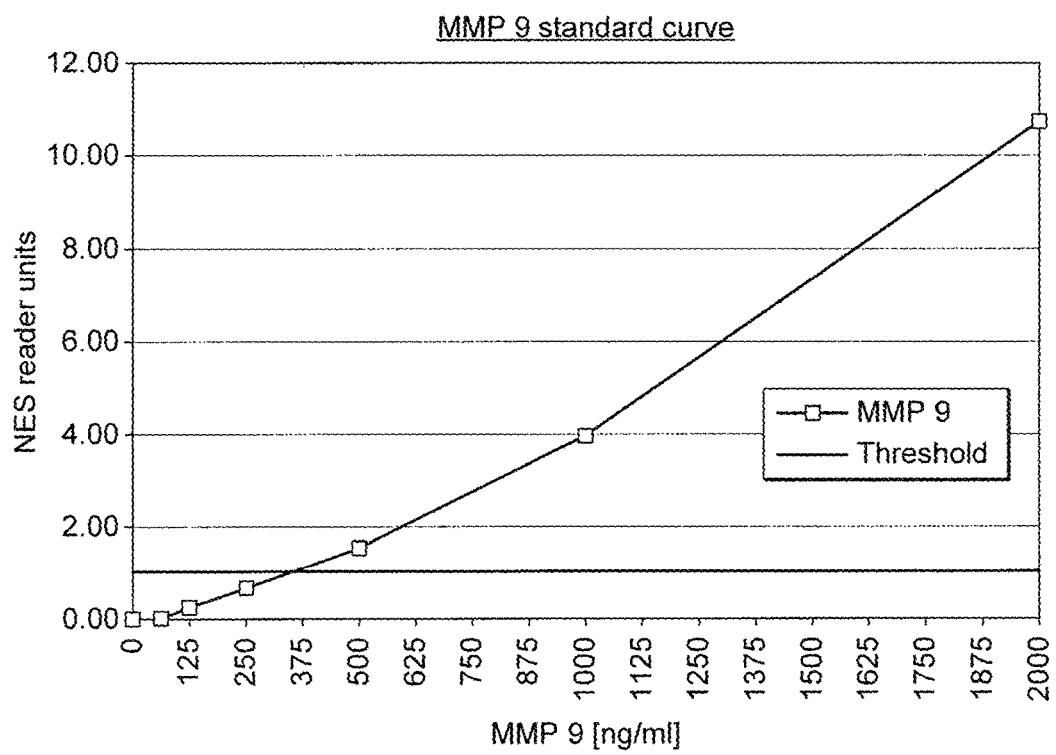
FIG. 9 shows results produced using an enzyme detection device according to the present invention to detect Matrix Metalloprotease-9 (MMP-9) activity using a first indicator molecule.

FIG. 9 demonstrates the sensitivity of the assay when run with spiked MMP-9 buffer samples. The detectable limit for MMP-9 was approximately 250-500 ng/ml with a sample volume of 20 µl. The reader units are displayed where a value above 1 was deemed a positive result.

Example 3

A Reverse ELTABA Platform Utilizing a Synthetic Peptide Indicator Molecule Consisting of 3 Epitopes and a Cleavage Site for the Detection of Matrix Metalloprotease-9 (MMP-9) and Human Neutrophil Elastase (HNE)

A kit comprises the following components:—
1) A device for sample collection (e.g. for urine)
2) A chase buffer for re-hydrating the gold conjugate consisting of Tris buffer saline (TBS) at pH 8.0 and 1% TWEEN™20 (Polyoxyethylene (20) sorbitan monolaurate).
3) A lateral flow test-strip, which is mounted in a plastic case. The test strip has a hidden capture zone which comprises of polystreptavidin in the form of four pre-absorbent lines (PA lines), a second capture zone which comprises anti-DNP as a first test line across the flow-path of the test strip and a third capture zone which comprises anti chicken antibodies adsorbed as a control line across the flow-path of the test strip, downstream of the test line. There is an observation window in the plastic case through which to view the test and control line. There is also an integrated sample receiving pad, upstream of the first test line. In addition, the test strip has gold particles bearing anti-FITC dried into the test strip upstream of the sample-receiving pad, which can be reconstituted by the addition of a buffer in a second well that receives the chase buffer upstream of the gold conjugate pad.
4) A test tube, in which the sample collection device may be placed, together with the indicating molecule.
5) An indicator molecule (which may be incorporated in the sample collection device). The indicator molecule consists of a peptide containing a sequence of amino acids biased for MMP-9 i.e. GPQGIFGQ (SEQ ID NO:1), a sequence of amino acids biased for HNE i.e. GAAPVA (SEQ ID NO:2), a DNP that acts as a $2^{nd}$ capture site and finally a fluorescent label that is the detection site. The peptide carries a terminal biotin group, connected via a polyethylene glycol spacer/linker that is recognised by the polystreptavidin immobilised in the hidden capture zone.

The Test Strip

A test strip for the detection of protease activity in a fluid sample was constructed in accordance with the present invention, as described below. The assay is based on the cleavage of the indicator molecule in the presence of MMP-9 and HNE to yield a fragment that will bind to the test line. Various samples were tested with the strip including wound fluid samples for the detection of protease activity.

A. Preparation of Gold-Impregnated Conjugate Pads

Whatman Glass fiber pad (Whatman, Rapid 24Q, 12 mm×300 mm) was sprayed with anti FITC gold conjugate (Mologic) at OD4 and Chicken IgY Gold conjugate (Mologic) at OD2 diluted in gold drying buffer (50 mM Tris, 150 mM sodium chloride, 20 mM sodium Azide, 1% BSA, 10% Trehalose dihydrate, 1% TWEEN™20 (Polyoxyethylene (20) sorbitan monolaurate) at pH 8.0 ) at 0.6 µl /mm with the Isoflow dispenser (7 mm spray height). Processed conjugate band was dried in a tunnel dryer at 60 ° C. at a speed of 5 mm/sec. The dried gold conjugate-impregnated conjugate pads were stored in a sealed foil pouch with desiccant at room temperature.

B. Preparation of Antibody-Impregnated Nitrocellulose Membrane

All reagents were striped on Millipore HF090 membrane (Millipore, HF09004540, 40×300 mm) at a dispense rate of 0.05 µl/mm. PA lines comprised of 1 mg/ml Polystreptavidin (BBI, Dundee, 01041049L) at 10, 12, 14 and 16 mm from base of membrane, Test line Goat anti DNP (Bethyl labs, A150117A) at a concentration of 1 mg/ml at 23 mm from base of membrane and control line anti Chicken IgY (Lampire, 7455207) at a concentration of 0.5 mg/ml at 28 mm from base of membrane. Processed membrane was dried in a tunnel dryer at 60° C. at a speed of 10 mm/sec. The dried antibody-impregnated Nitrocellulose Membrane was stored dried in a sealed foil pouch with desiccant at room temperature.

C. Chase Buffer

Aq. Solution of 50 mM Tris, 150 mM sodium chloride, 20 mM sodium azide, 1% vol/vol TWEEN™20 (Polyoxyethylene (20) sorbitan monolaurate), at pH 8.0.

D. Card Assembly

A test card was assembled according to the following procedure and in accordance with FIG. 8 which specifies the exact longitudinal dimensions and position of each of the card components. Following preparation, the card was trimmed to obtain a plurality of strips for protease assay.

1. A 75×300 mm piece of clear plastic film with a release liner protected adhesive, serving as the back laminate (81) (G&L Precision Die Cutting, 28840) was placed on top of a worktable. The release liner was peeled to expose the adhesive side of the tape.
2. The reaction membrane (82), prepared as in section B, was attached on top of the adhesive side of the back cover (81), 16 mm from the lower end.
3. The impregnated conjugate pad (83), prepared as in section A was attached on top of the back cover (81) with 1 mm overlap on top of the reaction membrane (82).
4. The buffer pad (54, Whatman, CFS, 11×300 mm) was placed on top of the back cover (81) with 6 mm overlap on top of the conjugate pad (83).
5. The double sided tape (85, G&L Precision Die Cutting, GL-187) was attached over the conjugate pad (83) 15 mm from the lower end.
6. The sample receiving pad/blood separator membrane (86, Spectral SG membrane, Primecare) was placed over the tape (85) with cover removed, 15 mm from the lower end.
7. The absorbent pad (87, Gel blotting paper, Ahlstrom, grade 222, 23×300 mm) was placed on top of the upper side of the back cover (81) with a 3 mm overlap on top of the reaction membrane (82).

The card was trimmed to 4 mm width strips using an automated die cutter (Kinematic, 2360) and assembled into 2 well plastic housings (BBI Dundee, vision). The devices were closed using a pneumatic device clamp specifically manufactured for these devices at Mologic.

In the example described below, buffer standards were produced containing different concentrations of MMP-9 (Mologic) and HNE (Lee biotech, 342-40) ranging from 2000 ng/ml down to 7.8 ng/ml.

STEP 1: A sample of fluid (the test sample) was placed in a collection device with a defined amount of indicator molecule (400 pg/test). The collection device was rotated vigorously in order for the sample to mix sufficiently with the indicator molecule. This reaction mixture was incubated at ambient temperature for a defined period of time (e.g. 10 minutes).

STEP 2: At the end of the incubation period, a defined volume of liquid was dropped onto the sample receiving pad (86). The indicator molecule which was added to the sample prior to the incubation period was able to bind to the polystreptavin in the hidden capture zone via the $1^{st}$ capture region. Any MMP-9 and/or HNE present in the sample cleaved the indicator molecule at the cleavage site, allowing the release of the cleaved fragment from the hidden capture zone. The cleaved fragment migrated towards the anti-DNP test line where it was immobilised via the DNP capture site.

STEP 3: Once the sample had travelled through the test strip (82) aided by the absorbent pad (87) that acted as a reservoir, two drops of the chase buffer provided in the kit was added to a buffer pad (84) that made contact with and re-hydrated the dried anti-FITC attached to the gold particles. As the conjugated gold particles entered the hidden capture zone any intact indicator molecule bound to the pre-absorbent lines was labelled via the fluorescent label detection site. Those that had not bound to the intact indicator molecule in the hidden capture zone migrated down the strip and labelled any cleaved indicator molecule captured by the test line. A separate control system was used that comprised of chicken IgY attached to gold particles which bound to a Goat anti Chicken IgY control line. The presence of a line indicated that the test was complete.

The lines that were formed were assessed by their relative intensities. The presence of a test line and the presence of a full strength control line indicated that there was protease present in the test sample. A negative test line indicated a zero or low level of protease that was below the detectable limit. Stages in between these extremes indicated different levels of protease in the test sample. The intensity of the developed coloured lines was measured visually and with an NES Lateral flow device reader. A semi-quantitative scoring system with a scale of 0-10, in which 1 was the lowest detectable colour intensity and 10 was the highest observed colour intensity was used for the visual readings.

Figure 10:
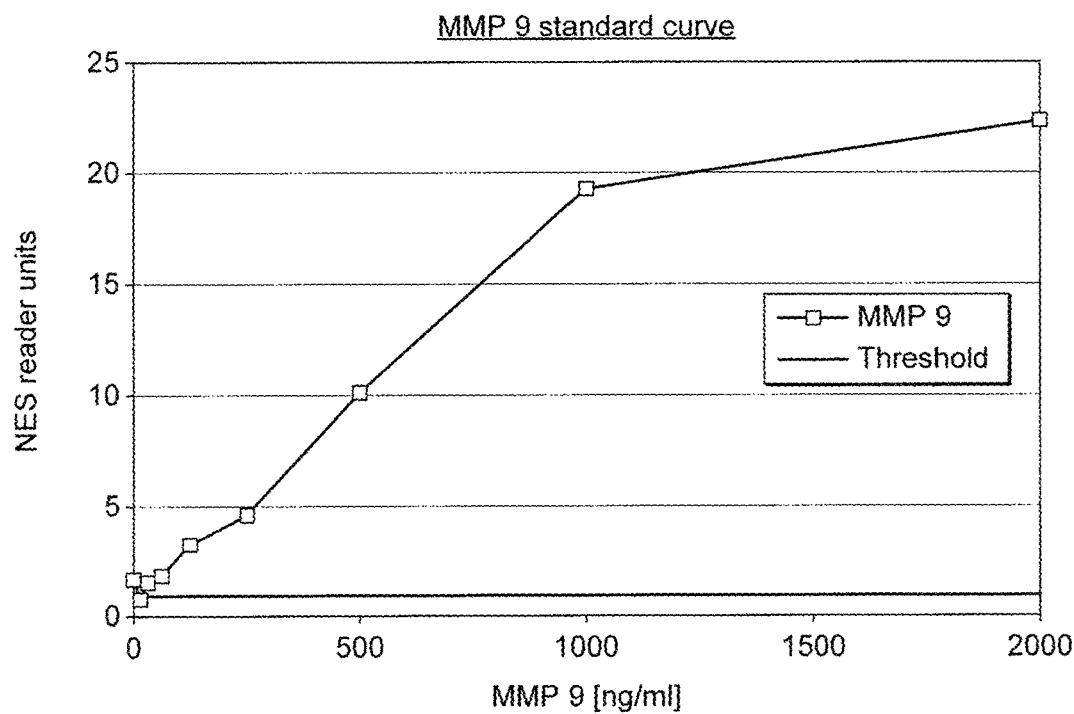
FIG. 10 shows results produced using an enzyme detection device according to the present invention to detect Matrix Metalloprotease-9 (MMP-9) activity using a second indicator molecule.

FIG. 10 demonstrates the sensitivity of the assay when run with spiked MMP-9 buffer samples. The detectable limit for MMP-9 was approximately 125-250 ng/ml with a sample volume of 30 µl. The reader units are displayed where a value above 1 was deemed a positive result.

Figure 11:
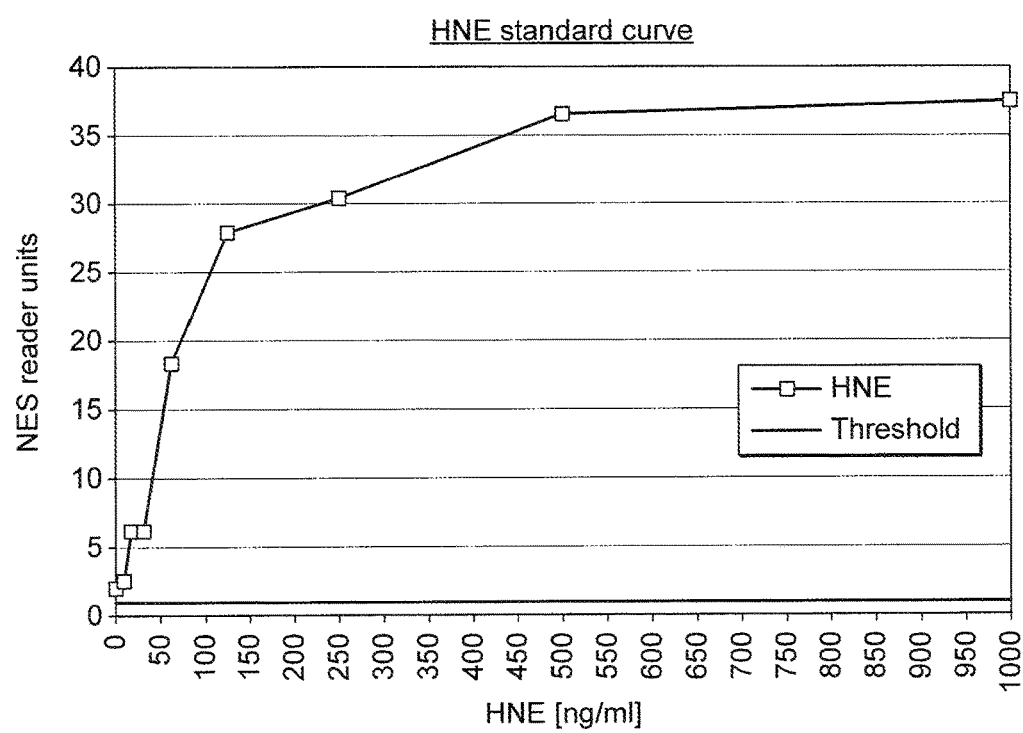
FIG. 11 shows results produced using an enzyme detection device according to the present invention to detect human neutrophil elastase (HNE) activity.

FIG. 11 demonstrates the sensitivity of the assay when run with spiked HNE buffer samples. The detectable limit for HNE was approximately 62.5-125 ng/ml with a sample volume of 30 µl. The reader units are displayed where a value above 1 was deemed a positive result.

Example 4

A Reverse ELTABA Platform Utilizing Synthetic Peptide Indicator Molecules Including Multiple Cleavage Sites for the Detection of Matrix Metalloprotease-9 (MMP-9)

Separate experiments utilising kits and test strips as described in Example 2 were carried out using the indicator molecule of Example 2 consisting of a peptide containing a sequence of amino acids including an MMP9 cleavage site, GPQGIFGQ (SEQ ID NO:1), and additional indicator molecules consisting of peptides containing 2, 3, 5 and 7 MMP9 cleavage sites. The indicator molecules with multiple MMP9 cleavage sites were otherwise the same as described in Example 2 with a first capture region (ALP) capable of binding to CF1060 at the PA lines, and a terminal biotin group connected via a polyethylene glycol spacer/linker. These experiments were carried out in order to test the sensitivity of the assay using indicator molecules having multiple cleavage sites.

The experiments were carried out in accordance with Steps 1 to 3 of Example 2 using buffer standards containing different concentrations of MMP9 ranging from 2000 ng/ml down to 31.25 ng/ml. The results are shown in Table 1 and FIG. 12.

TABLE 1

| ng/ml MMP9 | 1 CS | 2 CS | 3 CS | 5 CS | 7 CS |
| --- | --- | --- | --- | --- | --- |
| 0 | 0.00 | 0.00 | 0.00 | 0.21 | 1.34 |
| 31.25 | 0.00 | 0.68 | 0.00 | 1.04 | 2.27 |
| 62.5 | 0.00 | 0.32 | 0.00 | 1.36 | 2.81 |
| 125 | 0.00 | 0.57 | 0.00 | 2.14 | 3.25 |
| 250 | 0.00 | 1.99 | 0.92 | 5.01 | 6.19 |
| 500 | 1.93 | 3.48 | 3.84 | 9.93 | 9.31 |
| 1000 | 4.52 | 11.98 | 7.57 | 16.78 | 21.27 |
| 2000 | 8.00 | 11.76 | 10.49 | 20.48 | 25.34 |

Figure 12A:
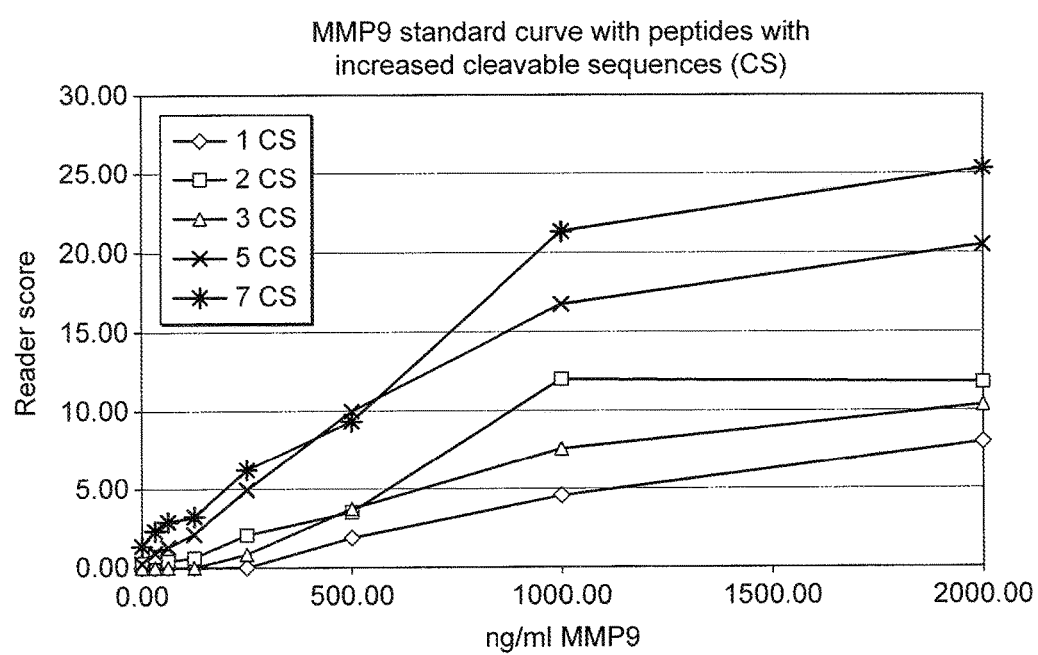
FIG. 12 shows results produced using an enzyme detection device according to the present invention wherein indicator molecules containing 1, 2, 3, 5 and 7 cleavage sites were used to detect MMP9 activity.
Figures 12B, 12C:
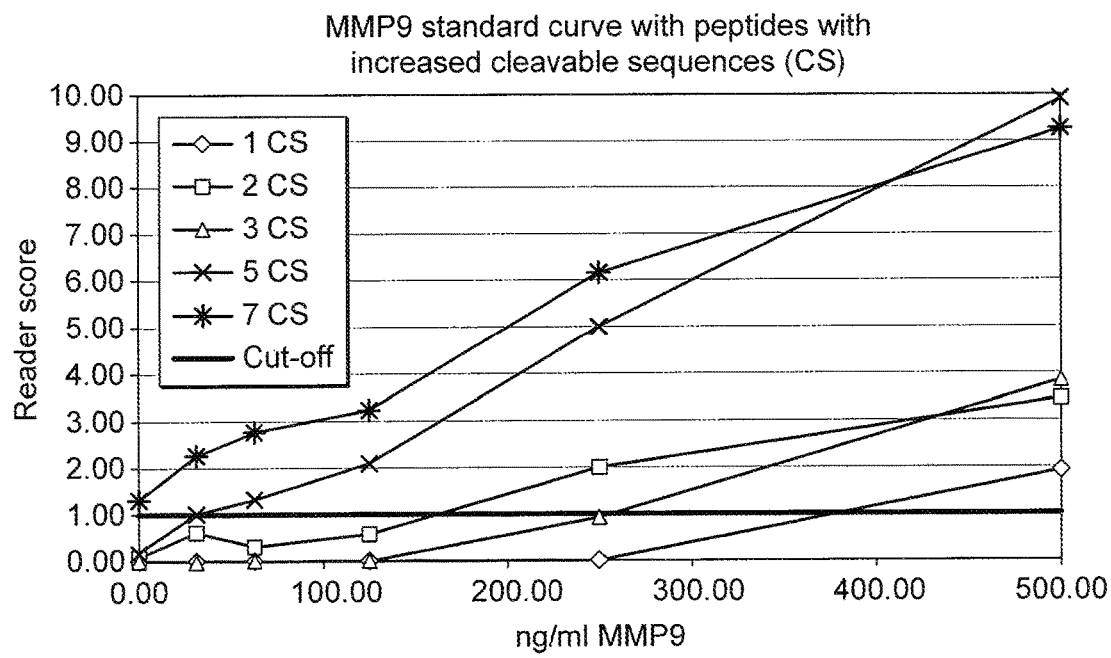

FIG. 12 shows the sensitivity of the assay when run with spiked MMP9 buffer samples and indicator molecules having 1, 2, 3, 5 and 7 MMP9 cleavage sites. The sensitivity increases from 250-500 ng/ml MMP9, seen with an indicator molecule having 1 cleavage site, to <31.25 ng/ml for an indicator molecule having 7 cleavage sites.

Example 5

A Reverse ELTABA Platform Utilizing Synthetic Peptide Indicator Molecules Including Multiple Cleavage Sites for the Detection of Matrix Metalloprotease-9 (MMP-9)

Separate experiments utilising kits and test strips as described in Example 3 were carried out using the indicator molecule of Example 3 consisting of a peptide containing a sequence of amino acids including an MMP9 cleavage site, GPQGIFGQ (SEQ ID NO:1), and additional indicator molecules consisting of peptides containing 2, 3, and 4 MMP9 cleavage sites. The indicator molecules with multiple MMP9 cleavage sites were otherwise the same as described in Example 3 with a terminal Biotin group forming a first capture region, a DNP acting as a second capture site within the detection region, and a FITC detection site. These experiments were carried out in order to test the sensitivity of the assay using indicator molecules having multiple cleavage sites.

The experiments were carried out in accordance with Steps 1 to 3 of Example 3 using buffer standards containing different concentrations of MMP9 ranging from 2000 ng/ml down to 31.25 ng/ml. The results are shown in Table 2 and FIG. 13.

TABLE 2

| ng/ml MMP9 | 1 CS | 2 CS | 3 CS | 4 CS |
| --- | --- | --- | --- | --- |
| 0 | 0.51 | 0.94 | 0.94 | 1.12 |
| 31.25 | 1.37 | 1.36 | 1.45 | 2.69 |
| 62.5 | 1.28 | 1.78 | 2.56 | 2.94 |
| 125 | 2.01 | 3.46 | 3.10 | 5.63 |
| 250 | 3.34 | 5.44 | 5.58 | 10.05 |
| 500 | 3.73 | 6.87 | 9.04 | 11.20 |
| 1000 | 4.33 | 5.48 | 11.62 | 16.30 |
| 2000 | 8.70 | 12.80 | 17.92 | 16.20 |

Figure 13A:
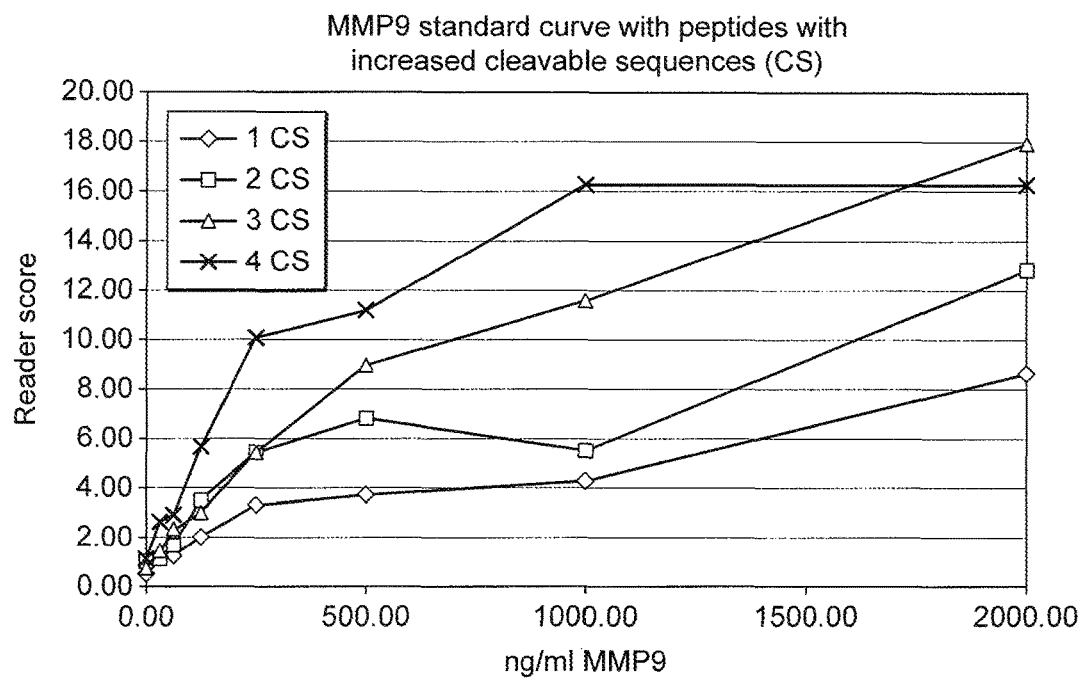
FIG. 13 shows the sensitivity of an enzyme detection device including an indicator molecule with 1, 2, 3 and 4 cleavage sites used to detect MMP9 activity.
Figure 13B:
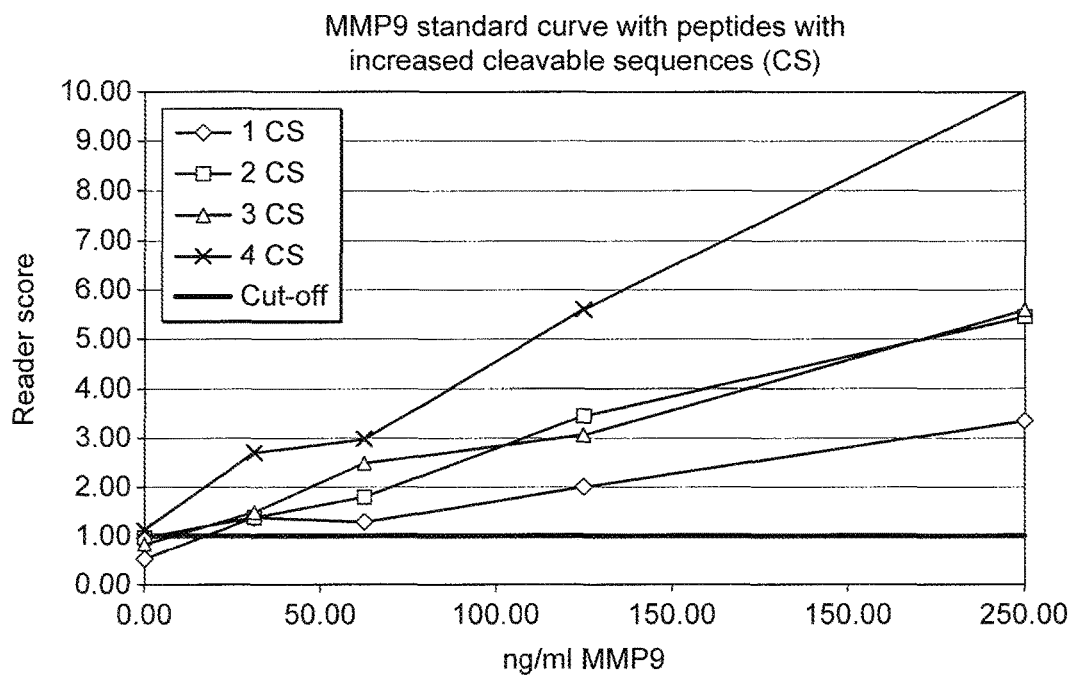

FIG. 13 shows the sensitivity of the assay when run with spiked MMP9 buffer samples and indicator molecules having 1, 2, 3, and 4 MMP9 cleavage sites. The cut-off with all indicator molecules was below <31.25 ng/ml, with the assay including the peptide having 4 cleavage sites appearing more sensitive. The signal intensity increased with increasing numbers of cleavage sites, particularly at the lower levels of MMP9 giving a more defined cut-off.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. Moreover, all aspects and embodiments of the invention described herein are considered to be broadly applicable and combinable with any and all other consistent embodiments, including those taken from other aspects of the invention (including in isolation) as appropriate. Various publications are cited herein, the disclosures of which are incorporated by reference in their entireties.

The invention claimed is:

1. An enzyme detection device for detecting the presence in a test sample of cleavage activity of an enzyme capable of cleaving a substrate, the device comprising:
 (i) an indicator molecule for adding to the test sample, said indicator molecule comprising
  (a) a cleavage site, which can be cleaved by said enzyme if said enzyme cleavage activity is present;
  (b) a first capture site; and
  (c) a detection region comprising a second capture site, wherein the cleavage site and first capture site form overlapping sites within a substrate region of the indicator molecule and wherein cleavage of the cleavage site results in release of a fragment of the indicator molecule comprising the detection region;
 (ii) a first capture zone to receive the test sample, wherein the first capture zone comprises first capture molecules capable of binding to the first capture site of the indicator molecule but not the cleaved fragment of the indicator molecule comprising the detection region and wherein the indicator molecule is captured by binding of the first capture site to the first capture molecules thereby substantially preventing any subsequent cleavage of the cleavage site by the enzyme; and
 (iii) a second capture zone to receive the test sample following contact of the test sample with the first capture zone, wherein the second capture zone comprises second capture molecules capable of binding to the second capture site of the indicator molecule, wherein the second capture zone is spatially separated from the first capture zone, and wherein detection of any cleaved indicator molecule via the detection region and bound via the second capture site to the second capture molecules, indicates the presence of cleavage activity of the enzyme in the test sample.

2. The device of claim 1 wherein the enzyme to be detected is selected from the group consisting of oxidoreductases, hydrolases and lyases, and include the subcategories of protease, peptidase, lipase, nuclease, carbohydrase, phosphatase, sulphatase, neuraminidase, esterase, DNAse, and RNAse.

3. The device of claim 1 wherein the enzyme to be detected is a matrix metalloprotease or human neutrophil-derived elastase.

4. The device of claim 1 wherein the indicator molecule comprises multiple cleavage sites and wherein cleavage at any one of the cleavage sites results in release of a fragment of the indicator molecule comprising the detection region.

5. The device of claim 1 wherein the first capture site of the indicator molecule and the first capture molecule present in the first capture zone of the device are two halves of a binding pair wherein the binding pair is selected from the group consisting of an antigen and an antibody or antigen binding fragment thereof; biotin and avidin, streptavidin, neutravidin or captavidin; an immunoglobulin or appropriate domain thereof and protein A or G; a carbohydrate and a lectin; complementary nucleotide sequences; a ligand and a receptor molecule; a hormone and hormone binding protein; an enzyme cofactor and an enzyme; an enzyme inhibitor and an enzyme; a cellulose binding domain and cellulose fibres; immobilised aminophenyl boronic acid and cis-diol bearing molecules; and xyloglucan and cellulose fibres and analogues, derivatives and fragments thereof.

6. The device of claim 1 wherein a plurality of indicator molecules may bind to each first capture molecule.

7. The device of claim 1 wherein the second capture site and second capture molecules are two halves of a binding pair wherein the binding pair is selected from the group consisting of an antigen and an antibody or antigen binding fragment thereof; biotin and avidin, streptavidin, neutravidin or captavidin; an immunoglobulin or appropriate domain thereof and protein A or G; a carbohydrate and a lectin; complementary nucleotide sequences; a ligand and a receptor molecule; a hormone and hormone binding protein;
 an enzyme cofactor and an enzyme; an enzyme inhibitor and an enzyme; a cellulose binding domain and cellulose fibres; immobilised aminophenyl boronic acid and cis-diol bearing molecules; and xyloglucan and cellulose fibres and analogues, derivatives and fragments thereof.

8. The device of claim 1 additionally comprising a reporter molecule bound or capable of binding to the detection region of the indicator molecule.

9. The device of claim 8 wherein the reporter molecule binds to the detection region via the second capture site, wherein binding of the reporter molecule to the second capture site does not impair the ability of the second capture site to bind second capture molecules.

10. The device of claim 8 wherein the reporter molecule comprises a reporter moiety selected from the group consisting of a gold particle; a chromogen; a luminescent compound; a fluorescent molecule; a radioactive compound; a visible compound; a liposome or other vesicle containing signal producing substances; an electroactive species; or a combination of enzyme and its substrate.

11. The device of claim 8 wherein binding of the reporter molecule to the detection region is indirect and mediated by an adaptor capable of simultaneously binding the detection region and the reporter molecule.

12. The device of claim 8 wherein multiple reporter molecules may bind to each indicator molecule.

13. The device of claim 1 wherein the device is a flow device, and the first capture zone and second capture zone are present at sequential locations along a chromatographic medium.

14. A method for detecting the presence in a test sample of an enzyme capable of cleaving a substrate, the method comprising the steps of:
- (i) providing an enzyme detection device of claim 1;
- (ii) providing a test sample;
- (iii) adding the indicator molecules of the device to the test sample under conditions in which the enzyme, if present, can cleave the substrate region;
- (iv) bringing the test sample into contact with the first capture molecules of the device such that any intact indicator molecules, if present, are bound to the first capture molecules within the first capture zone and wherein binding of the indicator molecules to the first capture molecules substantially prevents any subsequent cleavage of the cleavage site of the indicator molecule by the enzyme;
- (v) bringing the test sample into contact with the second capture molecules of the device such that any fragments of cleaved indicator molecule comprising the detection region are bound, via the second capture site, by the second capture molecules; and
- (vi) detecting the presence or absence or level of fragments of cleaved indicator molecule comprising the detection region in the second capture zone via the detection region in order to determine the presence of enzyme in the test sample.

15. The method of claim 14 wherein detection of the intact indicator molecule, or cleaved fragment thereof present in the second capture zone, is carried out by the addition of a reporter molecule capable of binding to the detection region.

16. The method of claim 14 wherein the presence of reporter molecules bound to cleaved fragments of indicator molecules located within the second capture zone indicates that an enzyme capable of cleaving the cleavage site of the indicator molecule is present within the test sample.

17. The method of claim 14 wherein the presence of reporter molecules in the first capture zone but not in the second capture zone indicates that no enzyme is present in the test sample.

18. A method of determining the amount of an enzyme capable of cleaving a substrate in a first sample relative to the amount of said enzyme in one or more additional samples comprising the steps of:
- (i) providing the enzyme detection device of claim 1;
- (ii) providing a first sample;
- (iii) adding the indicator molecules of the device to the first sample under conditions in which the enzyme, if present, can cleave the cleavage site;
- (iv) bringing the first sample into contact with the first capture molecules of the device such that any intact indicator molecules, if present, are bound to the first capture molecules within the first capture zone and wherein binding of the indicator molecules to the first capture molecules substantially prevents any subsequent cleavage of the cleavage site of the indicator molecule by the enzyme;
- (v) bringing the first sample into contact with the second capture molecules of the device such that any fragments of cleaved indicator molecule comprising the detection region are bound, via the second capture site, by the second capture molecules;
- (vi) detecting the presence and level of intact indicator molecule in the first capture zone and the presence and level of cleaved indicator molecule in the second capture zone;
- (vii) repeating steps (i) to (vi) for the one or more additional samples;
- (viii) comparing the levels obtained for the first and one or more additional samples in order to determine the relative levels of enzyme present in each sample.

19. The method of claim 18 wherein at least one of the samples used for comparison comprises a known amount of enzyme.

* * * * *

SEQUENCE LISTING

<160> NUMBER OF SEQ ID NOS: 2

<210> SEQ ID NO 1
<211> LENGTH: 8
<212> TYPE: PRT
<213> ORGANISM: Artificial sequence
<220> FEATURE:
<223> OTHER INFORMATION: Synthetic peptide

<400> SEQUENCE: 1

Gly Pro Gln Gly Ile Phe Gly Gln

```
<210> SEQ ID NO 2
<211> LENGTH: 6
<212> TYPE: PRT
<213> ORGANISM: Artificial sequence
<220> FEATURE:
<223> OTHER INFORMATION: Synthetic peptide

<400> SEQUENCE: 2

Gly Ala Ala Pro Val Ala
1               5
```